(12) United States Patent
Yokoyama et al.

(10) Patent No.: US 9,732,036 B2
(45) Date of Patent: Aug. 15, 2017

(54) COMPOUND HAVING CARBAZOLE RING STRUCTURE, AND ORGANIC ELECTROLUMINESCENT DEVICE

(75) Inventors: Norimasa Yokoyama, Tokyo (JP); Makoto Nagaoka, Tsukuba (JP); Kazunori Togashi, Tokyo (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 772 days.

(21) Appl. No.: 13/391,956

(22) PCT Filed: Aug. 25, 2010

(86) PCT No.: PCT/JP2010/005237
§ 371 (c)(1),
(2), (4) Date: Feb. 23, 2012

(87) PCT Pub. No.: WO2011/024451
PCT Pub. Date: Mar. 3, 2011

(65) Prior Publication Data
US 2012/0175599 A1 Jul. 12, 2012

(30) Foreign Application Priority Data
Aug. 28, 2009 (JP) .................................. 2009-197656

(51) Int. Cl.
*H01L 51/50* (2006.01)
*C07D 209/86* (2006.01)
(Continued)

(52) U.S. Cl.
CPC ......... *C07D 209/86* (2013.01); *C07D 209/88* (2013.01); *C07D 401/14* (2013.01);
(Continued)

(58) Field of Classification Search
None
See application file for complete search history.

(56) References Cited

U.S. PATENT DOCUMENTS 9,145,363 B2   9/2015 Yabunouchi et al.
2002/0045061 A1  4/2002 Hosokawa
(Continued)

FOREIGN PATENT DOCUMENTS

EP   2399906 A1   12/2011
EP   2497811 A2    9/2012
(Continued)

OTHER PUBLICATIONS

Mo Jun Xiong et al, "End-Capped Terfluorene Derivatives: Synthesis and Structure Functional Property Relationships," Australian Journal of Chemistry, vol. 60, No. 8, Jan. 1, 2007, pp. 608-614.
(Continued)

*Primary Examiner* — Gregory Clark
(74) *Attorney, Agent, or Firm* — Locke Lord LLP; James E. Armstrong, IV; Nicholas J. DiCeglie, Jr.

(57) ABSTRACT

[Problem] An organic compound of excellent characteristics is provided that exhibits excellent hole-injecting/transporting performance with electron blocking ability, and that has high stability in the thin-film state and high luminous efficiency, the organic compound being provided as material for an organic electroluminescent device having high efficiency and high durability. The invention also provides a high-efficient, high-durable organic electroluminescent device using the compound.
[Means for Resolution] The compound is of the following general formula having a carbazole ring structure. The organic electroluminescent device includes a pair of electrodes, and one or more organic layers sandwiched between
(Continued)

the pair of electrodes, and the compound is used as a constituent material of at least one organic layer.

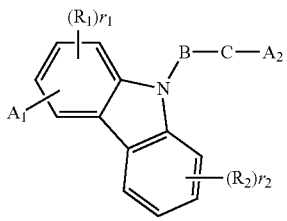

[Chemical Formula 1]

11 Claims, 6 Drawing Sheets

(51) Int. Cl.
| | |
|---|---|
| C07D 209/88 | (2006.01) |
| C07D 401/14 | (2006.01) |
| C07D 405/10 | (2006.01) |
| C07D 409/14 | (2006.01) |
| C07D 413/14 | (2006.01) |
| C07D 417/14 | (2006.01) |
| C07D 471/04 | (2006.01) |
| C09K 11/06 | (2006.01) |
| H01L 51/00 | (2006.01) |
| H05B 33/14 | (2006.01) |

(52) U.S. Cl.
CPC ......... *C07D 405/10* (2013.01); *C07D 409/14* (2013.01); *C07D 413/14* (2013.01); *C07D 417/14* (2013.01); *C07D 471/04* (2013.01); *C09K 11/06* (2013.01); *H01L 51/0061* (2013.01); *H05B 33/14* (2013.01); *C09K 2211/1029* (2013.01); *H01L 51/5012* (2013.01); *H01L 51/5016* (2013.01); *H01L 51/5056* (2013.01); *H01L 51/5096* (2013.01)

(56) References Cited

U.S. PATENT DOCUMENTS

| | | | |
|---|---|---|---|
| 2003/0137239 A1* | 7/2003 | Matsuura et al. | 313/503 |
| 2005/0208331 A1* | 9/2005 | Maeda | 428/690 |
| 2005/0225235 A1* | 10/2005 | Kim | C09K 11/06 313/504 |
| 2007/0122939 A1 | 5/2007 | Jeong et al. | |
| 2008/0014464 A1 | 1/2008 | Kawamura et al. | |
| 2008/0124572 A1 | 5/2008 | Mizuki et al. | |
| 2009/0302745 A1* | 12/2009 | Otsu | C07D 403/14 313/504 |
| 2010/0219404 A1 | 9/2010 | Endo et al. | |
| 2010/0301312 A1 | 12/2010 | Jinde et al. | |
| 2011/0278552 A1 | 11/2011 | Numata et al. | |
| 2011/0297924 A1 | 12/2011 | Yabunouchi et al. | |

FOREIGN PATENT DOCUMENTS

| | | | | |
|---|---|---|---|---|
| JP | 63-013047 A | 1/1988 | | |
| JP | 63-013048 A | 1/1988 | | |
| JP | 09-249876 | * | 9/1997 | ............ C09K 11/06 |
| JP | 09-249876 A | 9/1997 | | |
| JP | 11-154594 A | 6/1999 | | |
| JP | 2003-133075 A | 5/2003 | | |
| JP | 2004-345960 A | 12/2004 | | |
| JP | 2007-110097 A | 4/2007 | | |
| JP | 2007-158337 A | 6/2007 | | |
| JP | 2007-520470 A | 7/2007 | | |
| JP | 2008-135498 | * | 6/2008 | ............ H01L 51/50 |
| JP | 2008-135498 A | 6/2008 | | |
| JP | 2009-021335 A | 1/2009 | | |
| JP | 2009-076817 A | 4/2009 | | |
| KR | 2009-0112137 A | 10/2009 | | |
| KR | 10-2011-0117168 | 10/2011 | | |
| WO | WO-01/72927 A1 | 10/2001 | | |
| WO | WO-2005/090512 A1 | 9/2005 | | |
| WO | WO-2007/148660 A1 | 12/2007 | | |
| WO | WO-2009/041635 A1 | 4/2009 | | |
| WO | WO-2009/061156 A1 | 5/2009 | | |
| WO | WO-2009/081857 A1 | 7/2009 | | |
| WO | WO-2009/104488 A1 | 8/2009 | | |
| WO | WO-2010/095621 A1 | 8/2010 | | |
| WO | WO-2011/125680 A1 | 10/2011 | | |
| WO | WO-2011/139055 A2 | 11/2011 | | |
| WO | WO-2012/077902 A2 | 6/2012 | | |

OTHER PUBLICATIONS

Li Zhong Hui et al., "Synthesis and Functional Properties of End-Dendronized Oligo(9,9-diphenyl)fluorenes," Organic Letters, American Chemical Society, vol. 8, No. 7, Jan. 1, 2006, pp. 1499-1502.

Promarak V et al: "Synthesis and properties of stable amorphous hole-transporting molecules for electroluminescent devices," Tetrahedron Letters, vol. 47, No. 50, Dec. 11, 2006, pp. 8949-8952.

Jianping Lu et al: "Synthesis and Properties of Multi-Triarylamine-Substituted Carbazole-Based Dendrimers with an Oligothiophene Core for Potential Applications in Organic Solar Cells and Light-Emitting Diodes", Chemistry of Materials, American Chemical Society, vol. 18, Jan. 1, 2006, pp. 6194-6203.

Zhang X L et al: "Synthesis and functional properties of bis-dendronizd arylene amorphous molecular materials with high transition temperature," Synthetic Metals, vol. 160, No. 9-10, May 1, 2010, pp. 883-887.

Supplementary European Search Report dated Dec. 19, 2012, issued for the corresponding European patent application No. 10811508.0.

International Search Report dated Nov. 9, 2010, issued for PCT/JP2010/005237.

Office Action in corresponding application JP2011-528645 dated Aug. 5, 2014.

Office Action issued in corresponding Korean Patent Application No. KR 10-2012-7007872, dated Feb. 7, 2017 (Japanese translation).

\* cited by examiner

COMPOUND HAVING CARBAZOLE RING STRUCTURE, AND ORGANIC ELECTROLUMINESCENT DEVICE

TECHNICAL FIELD

The present invention relates to compounds suited for an organic electroluminescent device, a preferred self light-emitting device for various display devices, and to the device. Specifically, the invention relates to compounds having a carbazole ring structure, and organic electroluminescent devices using such compounds.

BACKGROUND ART

The organic electroluminescent device is a self-emitting device, and has been actively studied for their brighter, superior viewability and the ability to display clearer images compared with the liquid crystal device.

In 1987, C. W. Tang and colleagues at Eastman Kodak developed a laminated structure device using materials assigned with different roles, realizing practical applications of an organic electroluminescent device with organic materials. These researchers laminated tris(8-hydroxyquinoline) aluminum (an electron-transporting phosphor; hereinafter, simply $Alq_3$) and a hole-transporting aromatic amine compound, and injected the both charges into the phosphor layer to cause emission in order to obtain a high luminance of 1,000 $cd/m^2$ or more at a voltage of 10 V or less (see, for example, Patent Documents 1 and 2).

To date, various improvements have been made for practical applications of the organic electroluminescent device. In order to realize high efficiency and durability, various roles are further subdivided to provide an electroluminescence device that includes an anode, a hole injection layer, a hole transport layer, a light emitting layer, an electron transport layer, an electron injection layer, and a cathode successively formed on a substrate (see, for example, Non-Patent Document 1).

Further, there have been attempts to use triplet excitons for further improvements of luminous efficiency, and use of phosphorescent materials have been investigated (see, for example, Non-Patent Document 2).

The light emitting layer can be also fabricated by doping a charge-transporting compound, generally called a host material, with a phosphor or a phosphorescent material. As described in the foregoing lecture preprints, selection of organic materials in an organic electroluminescent device greatly influences various device characteristics, including efficiency and durability.

In an organic electroluminescent device, the charges injected from the both electrodes recombine at the light emitting layer to cause emission. The probability of hole-electron recombination can be improved and high luminous efficiency can be obtained by improving the hole injectability and the electron blocking performance of blocking the injected electrons from the cathode, and by thus confining the excitons generated in the light emitting layer. The role of the hole transport material is therefore important, and there is a need for a hole transport material that has high hole injectability, large hole mobility, high electron blocking performance, and high durability to electrons.

The aromatic amine derivatives described in Patent Documents 1 and 2 are known examples of the hole transport materials used for the organic electroluminescent device. These compounds include a compound known to have an excellent hole mobility of $10^{-3}$ cm/Vs or higher. However, the compound is insufficient in terms of electron blocking performance, and some of the electrons pass through the light emitting layer. Accordingly, improvements in luminous efficiency cannot be expected.

Arylamine compounds of the following formulae having a substituted carbazole structure (for example, Compounds A and B) are proposed as improvements over the foregoing compounds (see, for example, Patent Documents 3 and 4).

[Chemical Formula 1]

(Compound A)

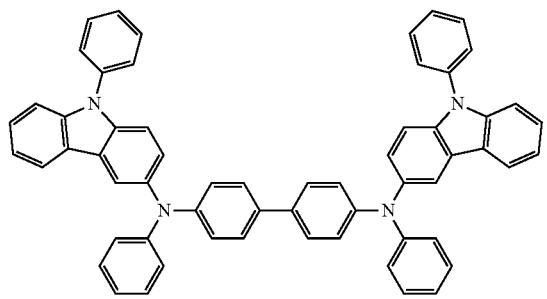

[Chemical Formula 2]

(Compound B)

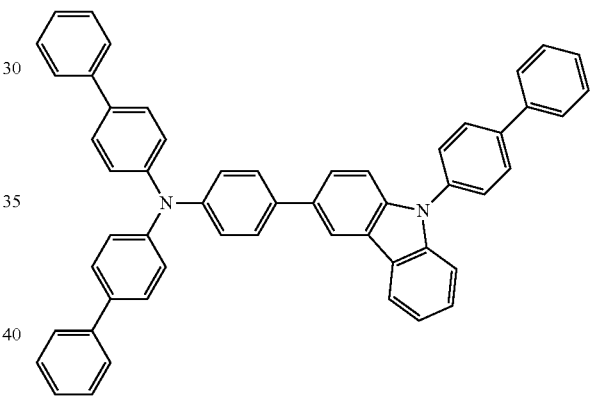

However, while the devices using these compounds for the hole injection layer or hole transport layer have improved luminous efficiency and the like, the luminous efficiency is still insufficient, and the device cannot be said to have a sufficiently low voltage and sufficient current efficiency. Further improvements of luminous efficiency are therefore needed.

CITATION LIST

Patent Documents

Patent Document 1: JP-A-8-48656
Patent Document 2: Japanese Patent No. 3194657
Patent Document 3: JP-A-2006-151979
Patent Document 4: WO2008/62636

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)

Non-Patent Document 3: Helvetica Chimica Acta., vol. 89, 1123 (2006)
Non-Patent Document 4: J. Org. Chem., 60, 7508 (1995)
Non-Patent Document 5: Synth. Commun., 11, 513 (1981)

SUMMARY OF THE INVENTION

Problems that the Invention is to Solve

It is an object of the present invention to provide an organic compound of excellent characteristics that exhibits excellent hole-injecting/transporting performance with electron blocking ability, and that has high stability in the thin-film state and high luminous efficiency, the organic compound being provided as material for an organic electroluminescent device having high efficiency and high durability. The invention also provides a high-efficient, high-durable organic electroluminescent device using the compound.

Some of the physical properties of the organic compound to be provided by the present invention include (1) good hole injection characteristics, (2) large hole mobility, (3) excellent electron blocking ability, (4) stability in the thin-film state, and (5) excellent heat resistance. Some of the physical properties of the organic electroluminescent device to be provided by the present invention include (1) high luminous efficiency and high power efficiency, (2) low turn on voltage, and (3) low actual driving voltage.

Means for Solving the Problems

In order to achieve the foregoing objects, the present inventors focused on the high hole transporting ability of an aromatic tertiary amine structure, the excellent electron blocking performance of a carbazole ring structure, and the excellent heat resistance and the thin-film stability of these structures, and produced various test organic electroluminescent devices using compounds designed and chemically synthesized to have a carbazole ring structure. The present invention was completed after thorough evaluations of the device characteristics.

Specifically, the present invention is a compound of the general formula (1) below having a carbazole ring structure. Further, the present invention is an organic electroluminescent device that includes a pair of electrodes and one or more organic layers sandwiched between the pair of electrodes, wherein the compound is used as a constituent material of at least one organic layer.

[Chemical Formula 3]

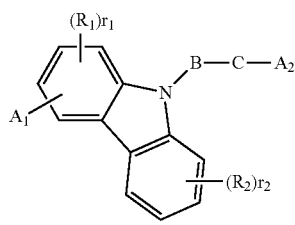

(1)

In the formula, R1 and R2 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r1 represents 0 or an integer of 1 to 3, r2 represents 0 or an integer of 1 to 4, A1 and A2 may be the same or different, A1 represents a monovalent group of the general formula (2) or (3) below, A2 represents one of the monovalent groups of the general formulae (2) to (7) below, B represents a divalent group of substituted or unsubstituted aromatic hydrocarbon, a divalent group of a substituted or unsubstituted aromatic heterocyclic ring, or a divalent group of substituted or unsubstituted condensed polycyclic aromatic, C represents a single bond, or a divalent group of substituted or unsubstituted aromatic hydrocarbon, a divalent group of a substituted or unsubstituted aromatic heterocyclic ring, or a divalent group of substituted or unsubstituted condensed polycyclic aromatic. Note that A1 and A2 do not simultaneously represent the general formula (2).

[Chemical Formula 4]

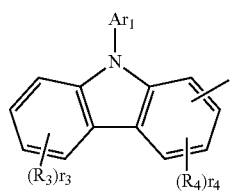

(2)

In the formula, R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r3 represents 0 or an integer of 1 to 4, r4 represents 0 or an integer of 1 to 3, and Ar1 represents substituted or unsubstituted aromatic hydrocarbon, a substituted or unsubstituted aromatic heterocyclic group, or substituted or unsubstituted condensed polycyclic aromatic.

[Chemical Formula 5]

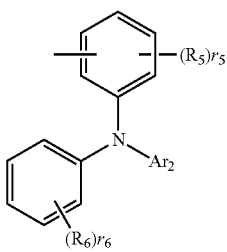

(3)

In the formula, R5 and R6 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r5 represents 0 or an integer of 1 to 4, r6 represents 0 or an integer of 1 to 5, and Ar2 represents substituted or unsubstituted aromatic hydrocarbon, a substituted or unsubstituted aromatic heterocyclic group, or substituted or unsubstituted condensed polycyclic aromatic.

[Chemical Formula 6]

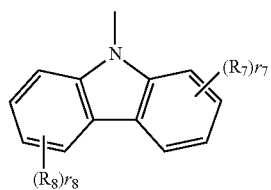

(4)

In the formula, R7 and R8 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r7 and r8 may be the same or different, and represent 0 or an integer of 1 to 4.

[Chemical Formula 7]

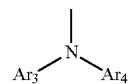

(5)

In the formula, Ar3 and Ar4 may be the same or different, and represent substituted or unsubstituted aromatic hydrocarbon, a substituted or unsubstituted aromatic heterocyclic group, or substituted or unsubstituted condensed polycyclic aromatic, and these groups may bind to each other via a single bond, substituted or unsubstituted methylene, an oxygen atom, or a sulfur atom to form a ring.

[Chemical Formula 8]

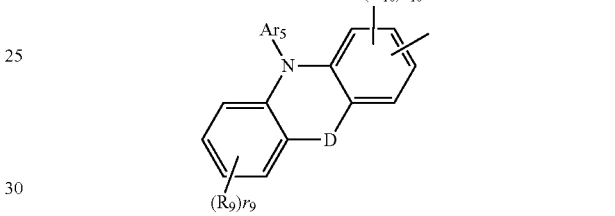

(6)

In the formula, R9 and R10 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r9 represents 0 or an integer of 1 to 4, r10 represents 0 or an integer of 1 to 3, Ar5 represents substituted or unsubstituted aromatic hydrocarbon, a substituted or unsubstituted aromatic heterocyclic group, or substituted or unsubstituted condensed polycyclic aromatic, and D represents substituted or unsubstituted methylene, an oxygen atom, or a sulfur atom.

[Chemical Formula 9]

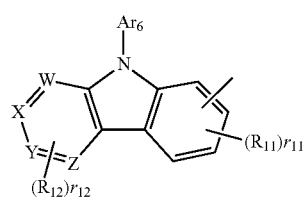

(7)

In the formula, R11 and R12 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r11 and r12 may be the same or different, and represent 0 or an integer of 1 to 3, Ar6 represents substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom. Here, only one of W, X, Y, and Z is a nitrogen atom, and, in this case, the nitrogen atom does not have the substituent R12.

Specific examples of "linear or branched alkyl having 1 to 6 carbon atoms", "cycloalkyl having 5 to 10 carbon atoms", and "linear or branched alkenyl having 2 to 6 carbon atoms" in the "linear or branched alkyl having 1 to 6 carbon atoms that may have a substituent", "cycloalkyl having 5 to 10 carbon atoms that may have a substituent", and "linear or branched alkenyl having 2 to 6 carbon atoms that may have a substituent" represented by R1 to R12 in general formulae (1) to (7) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl.

Specific examples of "substituent" in the "linear or branched alkyl having 1 to 6 carbon atoms that has a substituent", "cycloalkyl having 5 to 10 carbon atoms that has a substituent", and "linear or branched alkenyl having 2 to 6 carbon atoms that has a substituent" represented by R1 to R12 in general formulae (1) to (7) include a deuterium atom, a fluorine atom, a chlorine atom, cyano, nitro, phenyl, biphenylyl, terphenylyl, tetrakisphenyl, naphthyl, anthryl, fluorenyl, phenanthryl, indenyl, pyrenyl, and pyridoindolyl. These substituents may be further substituted.

Specific examples of "linear or branched alkyloxy having 1 to 6 carbon atoms" and "cycloalkyloxy having 5 to 10 carbon atoms" in the "linear or branched alkyloxy having 1 to 6 carbon atoms that may have a substituent" and "cycloalkyloxy having 5 to 10 carbon atoms that may have a substituent" represented by R1 to R12 in general formulae (1) to (7) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy.

Specific examples of "substituent" in the "linear or branched alkyloxy having 1 to 6 carbon atoms that has a substituent" and "cycloalkyloxy having 5 to 10 carbon atoms that has a substituent" represented by R1 to R12 in general formulae (1) to (7) include a deuterium atom, a fluorine atom, a chlorine atom, cyano, nitro, phenyl, biphenylyl, terphenylyl, tetrakisphenyl, naphthyl, anthryl, fluorenyl, phenanthryl, indenyl, pyrenyl, and pyridoindolyl. These substituents may be further substituted.

Specific examples of "aromatic hydrocarbon", "aromatic heterocyclic group", or "condensed polycyclic aromatic" in the "substituted or unsubstituted aromatic hydrocarbon", "a substituted or unsubstituted aromatic heterocyclic group", or "substituted or unsubstituted condensed polycyclic aromatic" represented by R1 to R12 or Ar1 to Ar6 in general formulae (1) to (7) include phenyl, biphenylyl, terphenylyl, naphthyl, anthryl, phenanthryl, fluorenyl, indenyl, pyrenyl, perylenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl.

Specific examples of "substituent" in the "substituted aromatic hydrocarbon", "substituted aromatic heterocyclic group", or "substituted condensed polycyclic aromatic" represented by R1 to R12 or Ar1 to Ar6 in general formulae (1) to (7) include a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, and phenethyloxy. These substituents may be further substituted. Further, these substituents may bind to each other via a single bond, substituted or unsubstituted methylene, an oxygen atom, or a sulfur atom to form a ring.

Specific examples of "aryloxy" in the "substituted or unsubstituted aryloxy" represented by R1 to R12 in general formulae (1) to (7) include phenoxy, biphenylyloxy, terphenylyloxy, naphthyloxy, anthryloxy, phenanthryloxy, fluorenyloxy, indenyloxy, pyrenyloxy, and perylenyloxy.

Specific examples of "substituent" in the "substituted aryloxy" represented by R1 to R12 in general formulae (1) to (7) include a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, and phenethyloxy. These substituents may be further substituted. Further, these substituents may bind to each other via a single bond, substituted or unsubstituted methylene, an oxygen atom, or a sulfur atom to form a ring.

Specific examples of "a divalent group of aromatic hydrocarbon", "a divalent group of an aromatic heterocyclic ring", and "a divalent group of condensed polycyclic aromatic" in the "divalent group of substituted or unsubstituted aromatic hydrocarbon", "divalent group of a substituted or unsubstituted aromatic heterocyclic ring", "divalent group of substituted or unsubstituted condensed polycyclic aromatic" represented by B and C in general formula (1) include phenylene, biphenylene, terphenylene, tetrakisphenylene, naphthylene, anthrylene, phenanthrylene, fluorenylene, phenanthrolylene, indenylene, pyrenylene, perylenylene, fluoranthenylene, triphenylenylene, pyridinylene, pyrimidinylene, quinolylene, isoquinolylene, indolylene, carbazolylene, quinoxalylene, benzoimidazolylene, pyrazolylene, naphthyridinylene, phenanthrolinylene, acridinylene, thienylene, benzothienylene, and dibenzothienylene.

Specific examples of "substituent" in the "divalent group of substituted aromatic hydrocarbon", "divalent group of a substituted aromatic heterocyclic ring", and "divalent group of substituted condensed polycyclic aromatic" represented by B and C in general formula (1) include a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, and phenethyloxy. These substituents may be further substituted. Further, these substituents may bind to each other via a single bond, substituted or unsubstituted methylene, an oxygen atom, or a sulfur atom to form a ring.

Among the compounds of general formula (1) having a carbazole ring structure, the compounds of the general formulae (1a), (1b), (1c), and (1d) below having a carbazole ring structure are preferably used for an organic electroluminescent device.

[Chemical Formula 8]

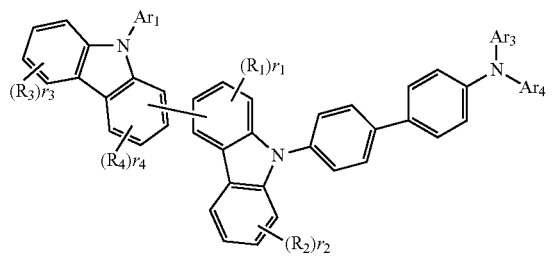

(1a)

In the formula, R1, R2, R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r1 and r4 may be the same or different, and represent 0 or an integer of 1 to 3, r2 and r3 may be the same or different, and represent 0 or an integer of 1 to 4, Ar1, Ar3, and Ar4 may be the same or different, and represent substituted or unsubstituted aromatic hydrocarbon, a substituted or unsubstituted aromatic heterocyclic group, or substituted or unsubstituted condensed polycyclic aromatic. Ar3 and Ar4 may bind to each other via a single bond, substituted or unsubstituted methylene, an oxygen atom, or a sulfur atom to form a ring.

[Chemical Formula 9]

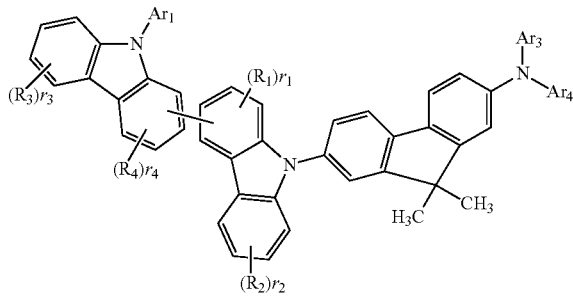

(1b)

In the formula, R1, R2, R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r1 and r4 may be the same or different, and represent 0 or an integer of 1 to 3, r2 and r3 may be the same or different, and represent 0 or an integer of 1 to 4, Ar1, Ar3, and Ar4 may be the same or different, and represent substituted or unsubstituted aromatic hydrocarbon, a substituted or unsubstituted aromatic heterocyclic group, or substituted or unsubstituted condensed polycyclic aromatic. Ar3 and Ar4 may bind to each other via a single bond, substituted or unsubstituted methylene, an oxygen atom, or a sulfur atom to form a ring.

[Chemical Formula 10]

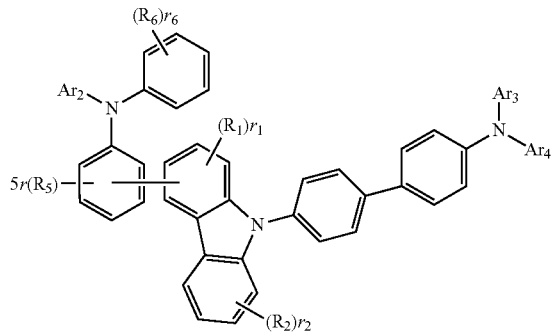

(1c)

In the formula, R1, R2, R5 and R6 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r1 represents 0 or an integer of 1 to 3, r2 and r5 may be the same or different, and represent 0 or an integer of 1 to 4, r6 represents 0 or an integer of 1 to 5, Ar1, Ar3, and Ar4 may be the same or different, and represent substituted or unsubstituted aromatic hydrocarbon, a substituted or unsubstituted aromatic heterocyclic group, or substituted or unsubstituted condensed polycyclic aromatic. Ar3 and Ar4 may bind to each other via a single bond, substituted or unsubstituted methylene, an oxygen atom, or a sulfur atom to form a ring.

[Chemical Formula 11]

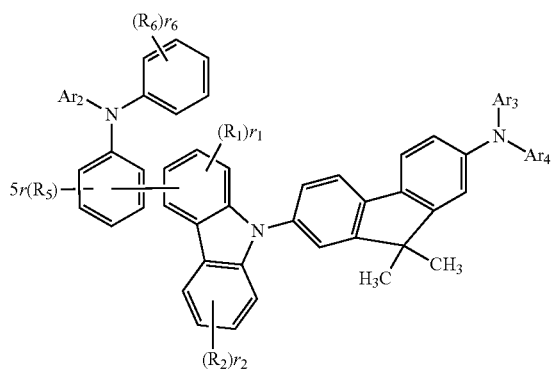

(1d)

In the formula, R1, R2, R5 and R6 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring. r1 represents 0 or an integer of 1 to 3, r2 and r5 may be the same or different, and represent 0 or an integer of 1 to 4, r6 represents 0 or an integer of 1 to 5, Ar2, Ar3, and Ar4 may be the same or different, and represent substituted or unsubstituted aromatic hydrocarbon, a substituted or unsubstituted aromatic heterocyclic group, or substituted or unsubstituted condensed polycyclic aromatic. Ar3 and Ar4 may bind to each other via a single bond, substituted or unsubstituted methylene, an oxygen atom, or a sulfur atom to form a ring.

The compounds of general formula (1) having a carbazole ring structure of the present invention are novel compounds, and have superior electron blocking ability and a more stable thin-film state compared to the conventional hole transport materials.

The compounds of general formula (1) having a carbazole ring structure of the present invention can be used as a constituent material of the hole injection layer and/or hole transport layer of an organic electroluminescent device (hereinafter, simply "organic EL device"). With the material having higher hole injectability, higher mobility, higher electron blocking performance and higher electron stability than the conventional materials, the excitons generated in the light emitting layer can be confined, and the probability of hole-electron recombination can be improved. This improves the luminous efficiency, and lowers driving voltage and thus improves the durability of the organic EL device.

The compound of general formula (1) having a carbazole ring structure of the present invention also can be used as a constituent material of the electron blocking layer of an organic EL device. With the material having an excellent electron blocking ability and superior hole transportability and higher stability in the thin-film state than the conventional materials, the driving voltage lowers and the current resistance improves while maintaining high luminous efficiency. As a result, the maximum emission luminance of the organic EL device improves.

The compound of general formula (1) having a carbazole ring structure of the present invention also can be used as a constituent material of the light emitting layer of an organic EL device. The material of the present invention has superior hole transportability and a wider band gap than the conventional materials, and can thus be used as the host material of the light emitting layer in order to form the light emitting layer by carrying a fluorescent material or phosphorescent material called a dopant. In this way, an organic EL device can be realized that has a low driving voltage and improved luminous efficiency.

The organic EL device of the present invention uses the compound having a carbazole ring structure, wherein the compound has greater hole mobility and superior electron blocking ability than the conventional hole transport materials while having a stable thin-film state. In this way, high efficiency and high durability are realized.

Advantage of the Invention

The compound having a carbazole ring structure of the present invention is useful as a constituent material of the hole injection layer, hole transport layer, electron blocking layer, or the light emitting layer of an organic EL device. The compound has an excellent electron blocking ability, and excels in heat resistance while having a stable thin-film state. The organic EL device of the present invention has high luminous efficiency and high power efficiency, and can thus lower the actual driving voltage of the device. Further, the turn on voltage can be reduced to improve durability.

MODE FOR CARRYING OUT THE INVENTION

Figure 1:
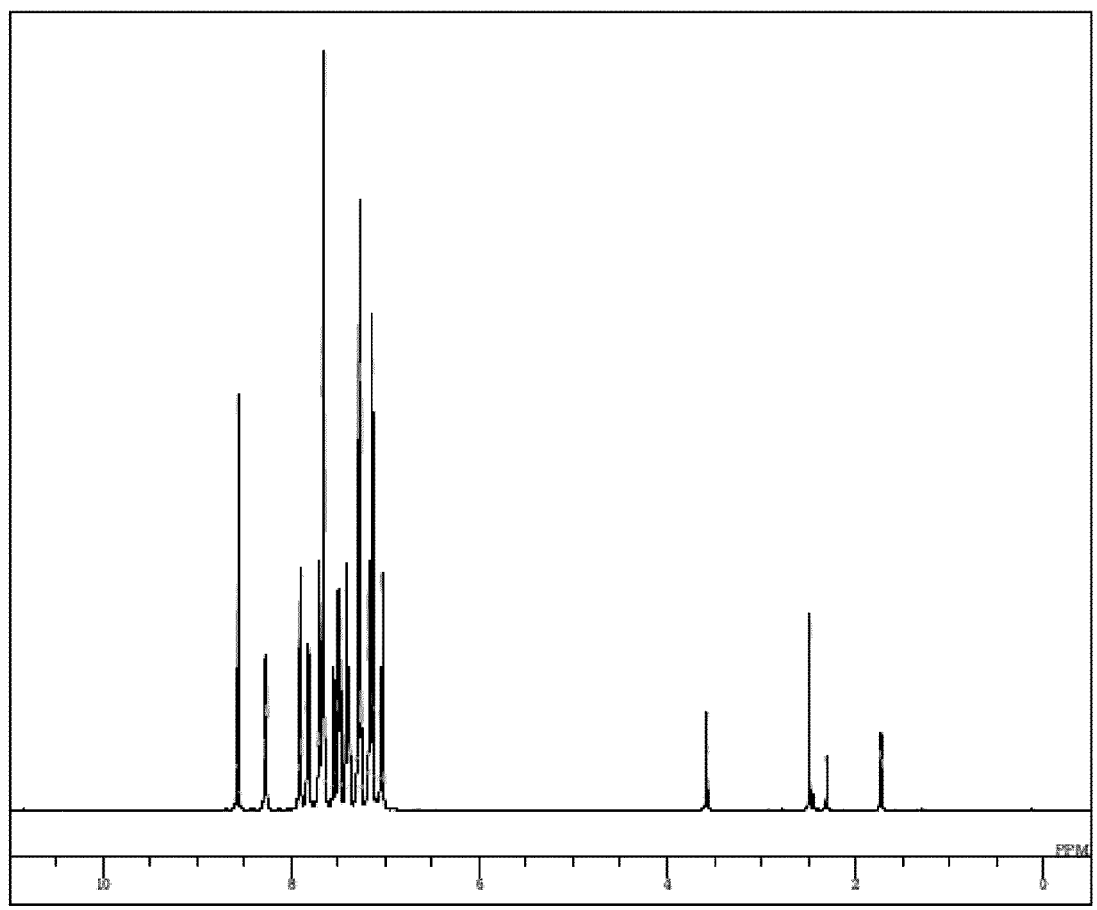
FIG. 1 is a 1H-NMR chart of the compound of Example 1 of the present invention (Compound 8).

The compounds having a carbazole ring structure of the present invention are novel compounds, and may be synthesized, for example, as follows. First, 3-bromo-9-arylcarbazole is synthesized by the bromination of a carbazole substituted with an aryl group at the corresponding ninth position, using, for example, N-bromosuccinimide (see, for example, Non-Patent Document 3). The boronic acid or borate synthesized by the reaction of the resulting bromo compound with compounds such as pinacolborane and bis (pinacolato)diboron (see, for example, Non-Patent Document 4) can then be reacted with various halogeno-9H-carbazoles in a cross-coupling reaction such as Suzuki coupling (see, for example, Non-Patent Document 5) to synthesize (N-aryl-9'H-carbazol-3'-yl)-9H-carbazole. A compound having a carbazole ring structure can then be synthesized by a condensation reaction, such as the Ullmann reaction, between the (N-aryl-9'H-carbazol-3'-yl)-9H-carbazole and aryl halides substituted with various diarylamino groups.

The following presents specific examples of preferred compounds among the compounds of general formula (1) having a carbazole ring structure. The present invention, however, is not restricted to these compounds.

[Chemical Formula 10]

(Compound 8)

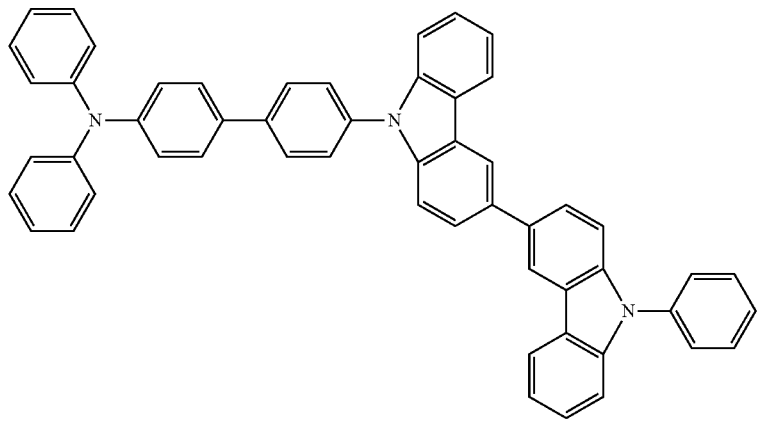

[Chemical Formula 11]

(Compound 9)

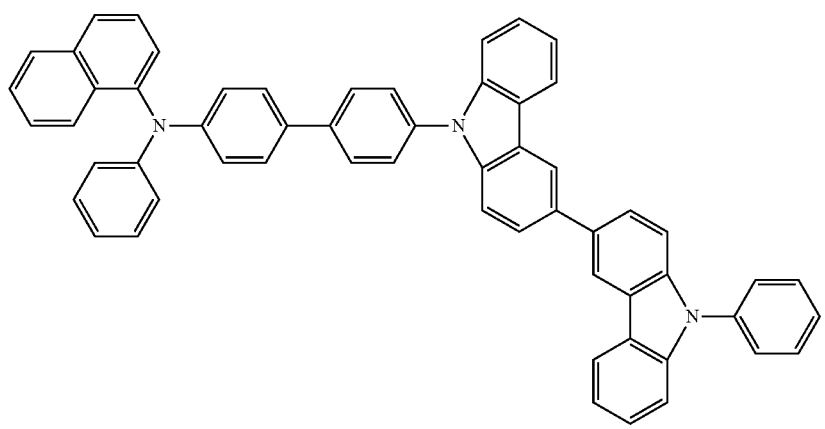

-continued
[Chemical Formula 12]
(Compound 10)
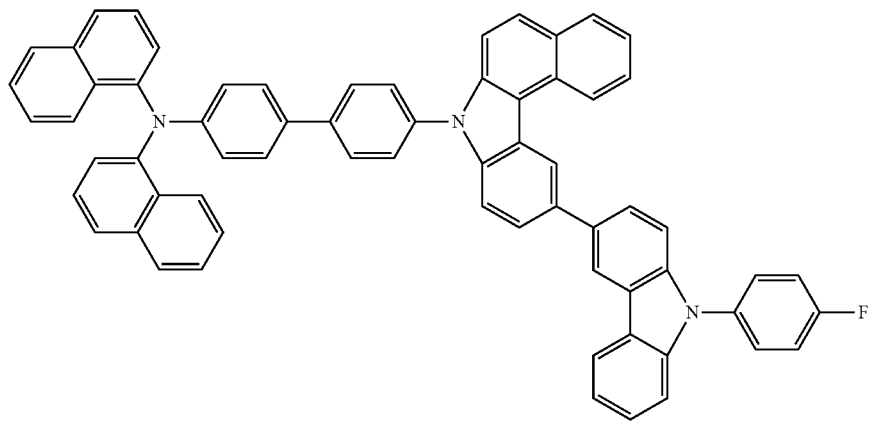
[Chemical Formula 13]
(Compound 11)
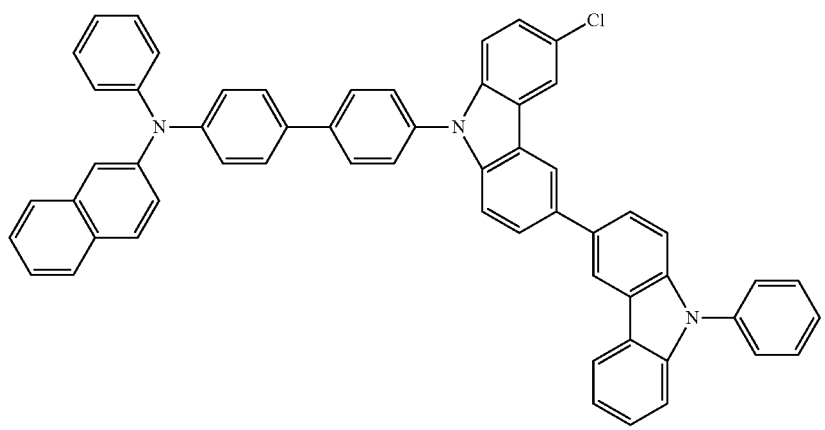
[Chemical Formula 14]
(Compound 12)
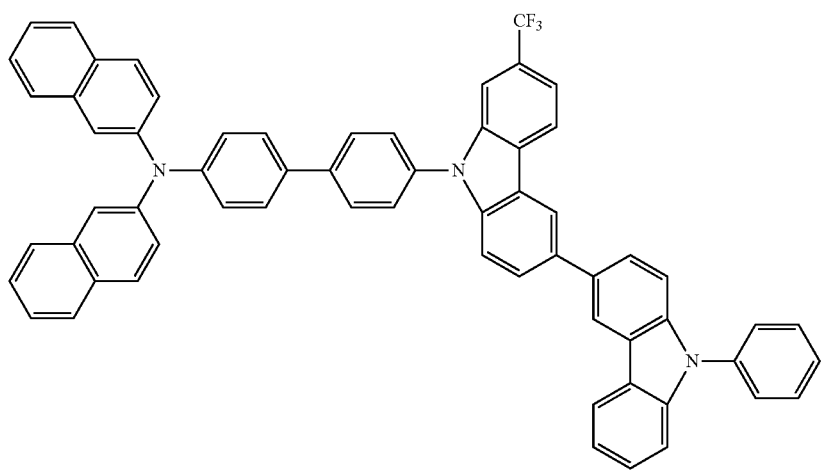

-continued
[Chemical Formula 15]
(Compound 13)
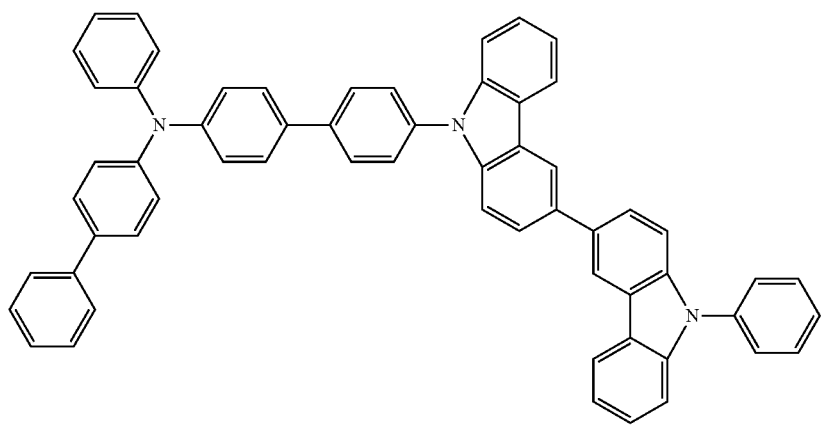
[Chemical Formula 16]
(Compound 14)
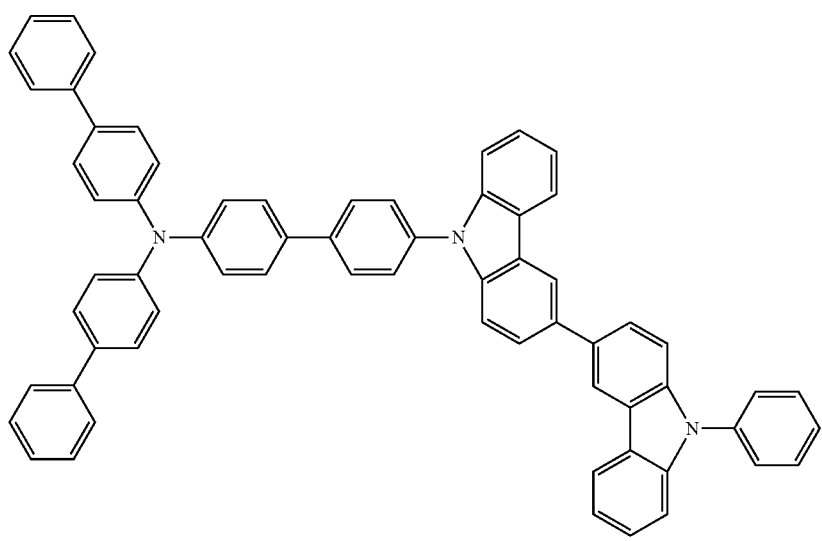
[Chemical Formula 17]
(Compound 15)
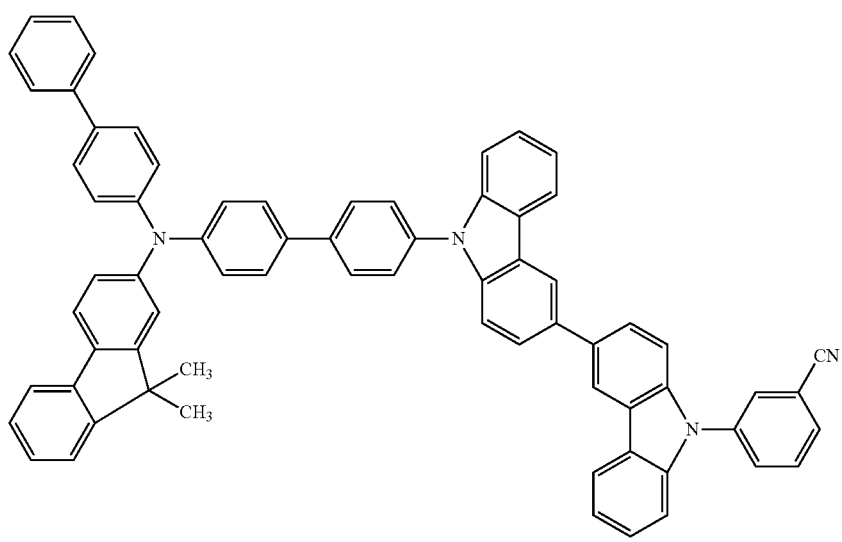

[Chemical Formula 18]
(Compound 16)
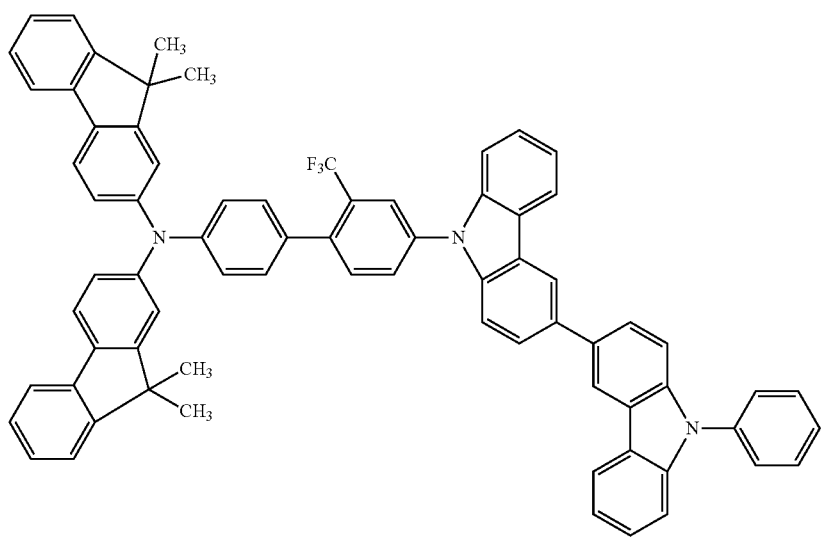
[Chemical Formula 19]
(Compound 17)
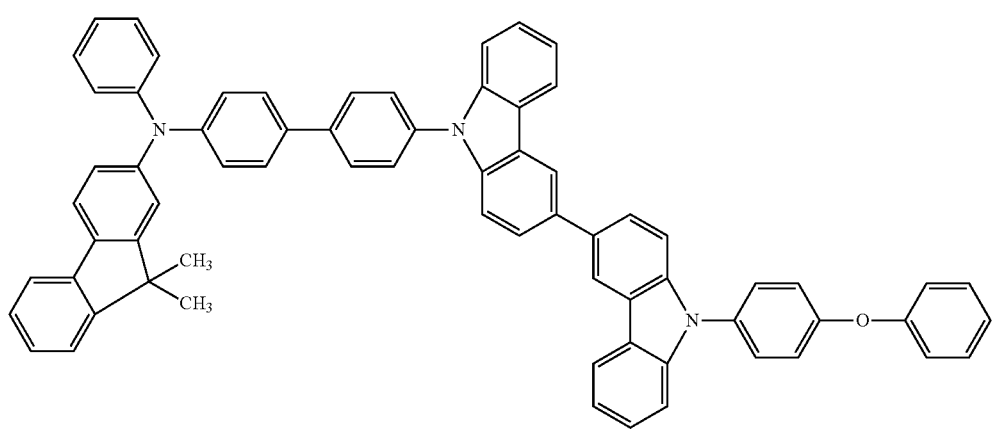
[Chemical Formula 20]
(Compound 18)
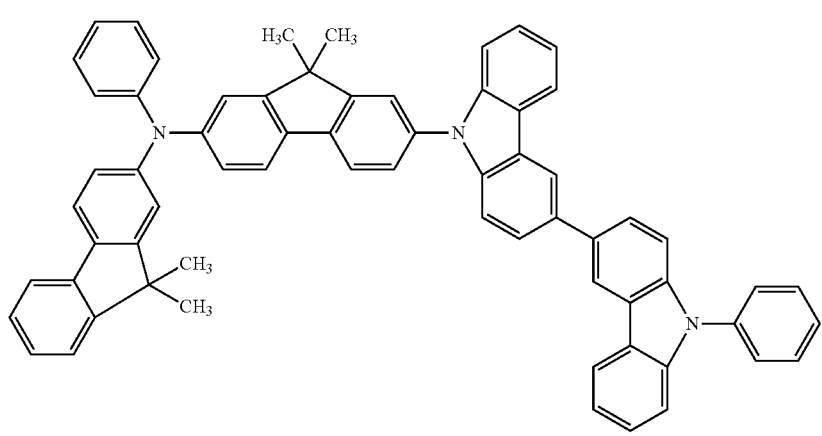

-continued
[Chemical Formula 21]
(Compound 19)
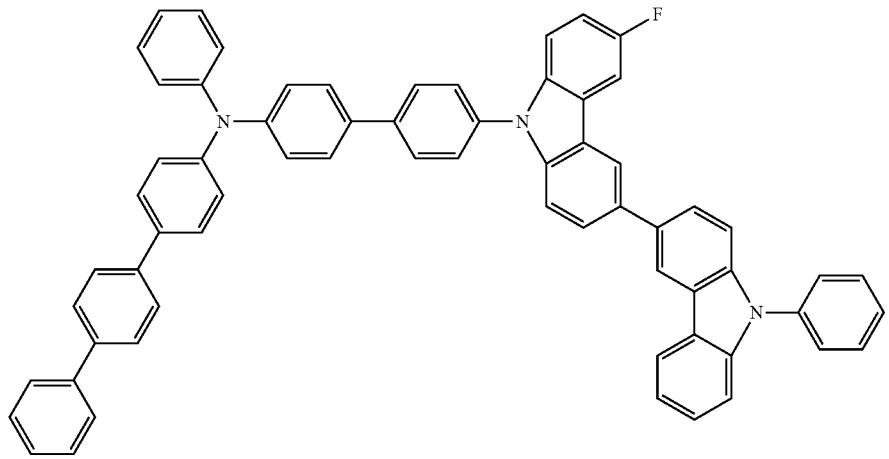
[Chemical Formula 22]
(Compound 20)
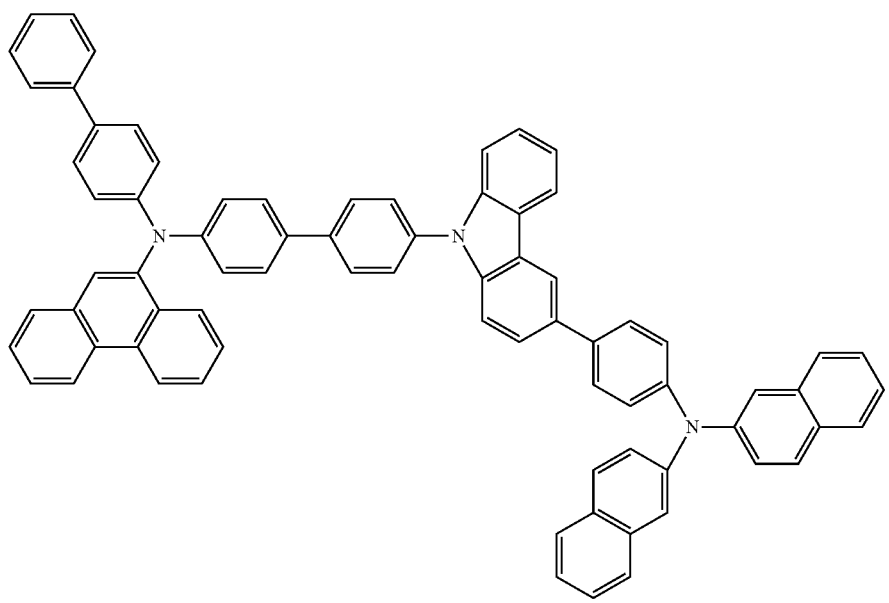
[Chemical Formula 23]
(Compound 21)
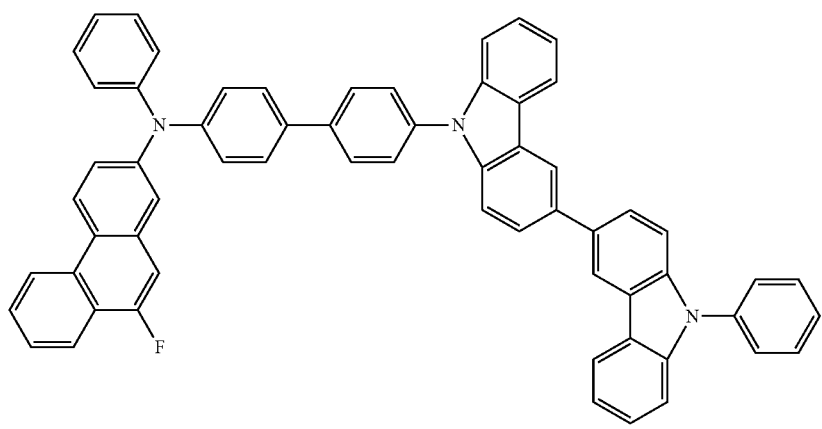

-continued
[Chemical Formula 24]
(Compound 22)
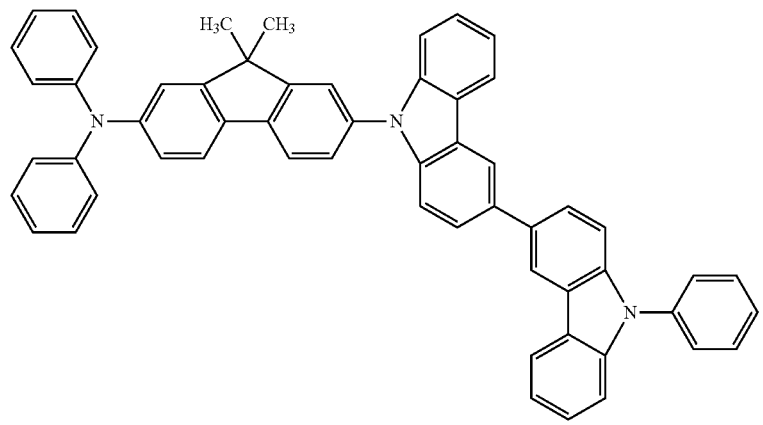
[Chemical Formula 25]
(Compound 23)
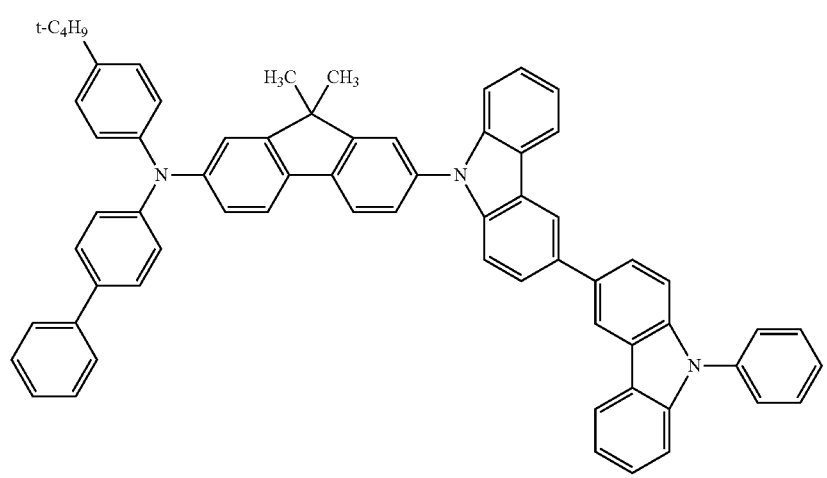
[Chemical Formula 26]
(Compound 24)
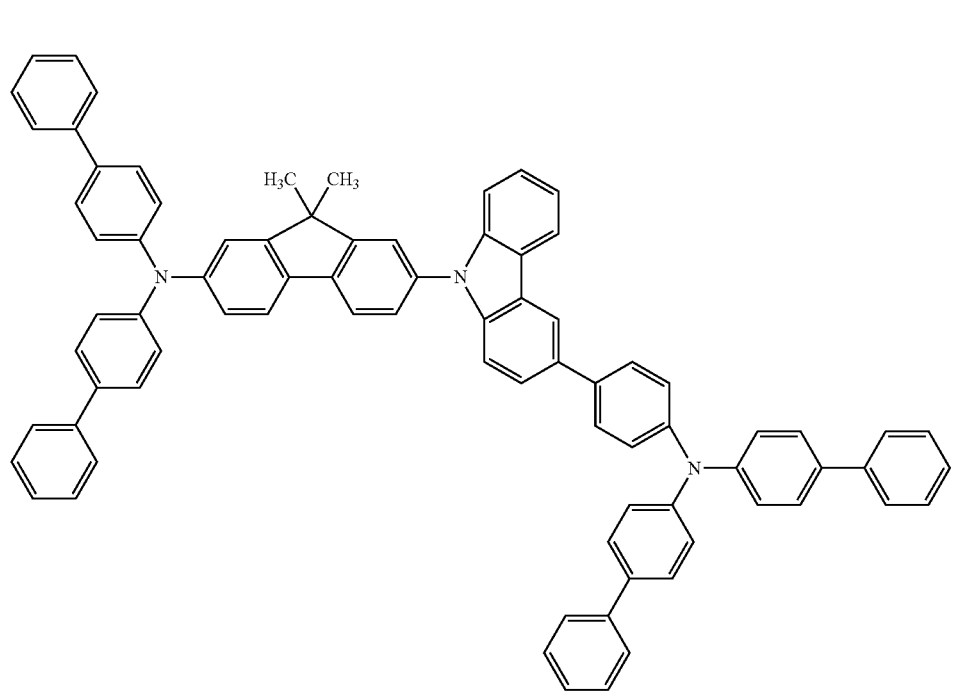

-continued
[Chemical Formula 27]
(Compound 25)
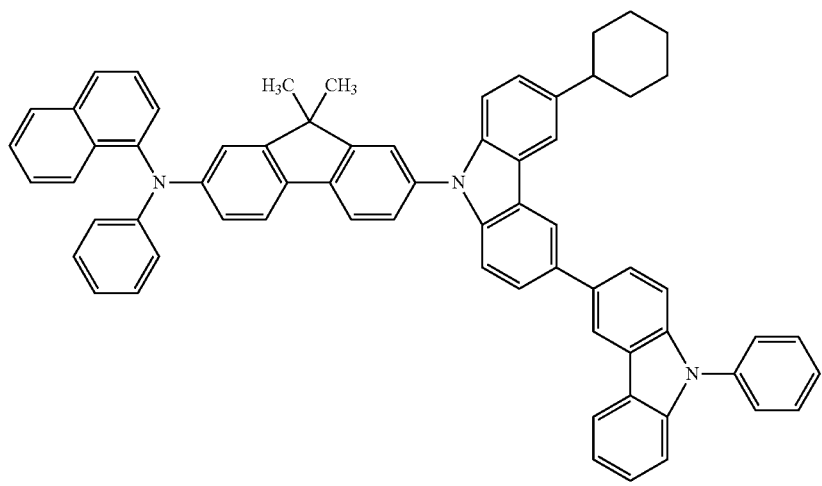
[Chemical Formula 28]
(Compound 26)
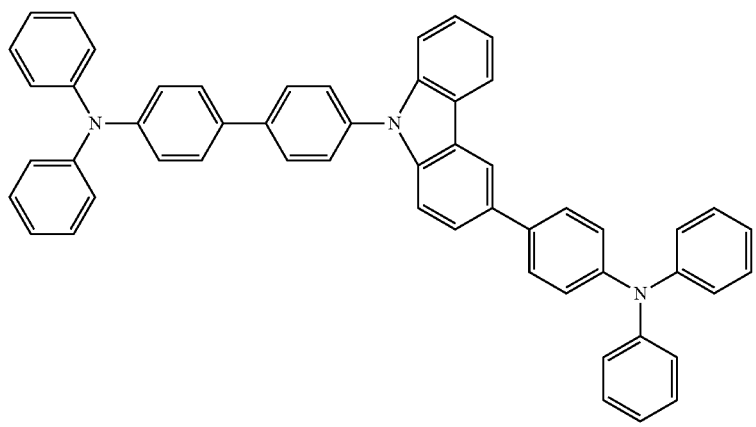
[Chemical Formula 29]
(Compound 27)
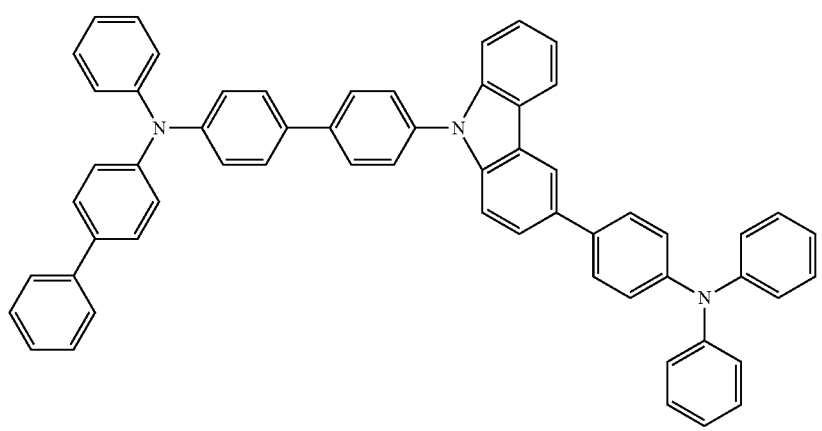

[Chemical Formula 30]
(Compound 28)
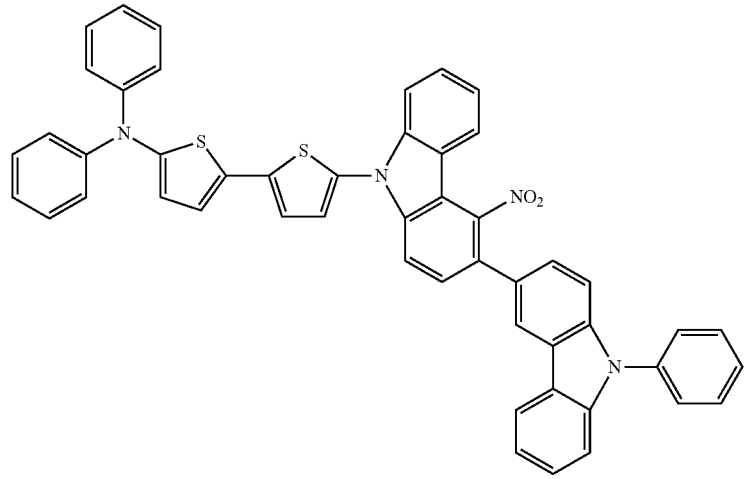
[Chemical Formula 31]
(Compound 29)
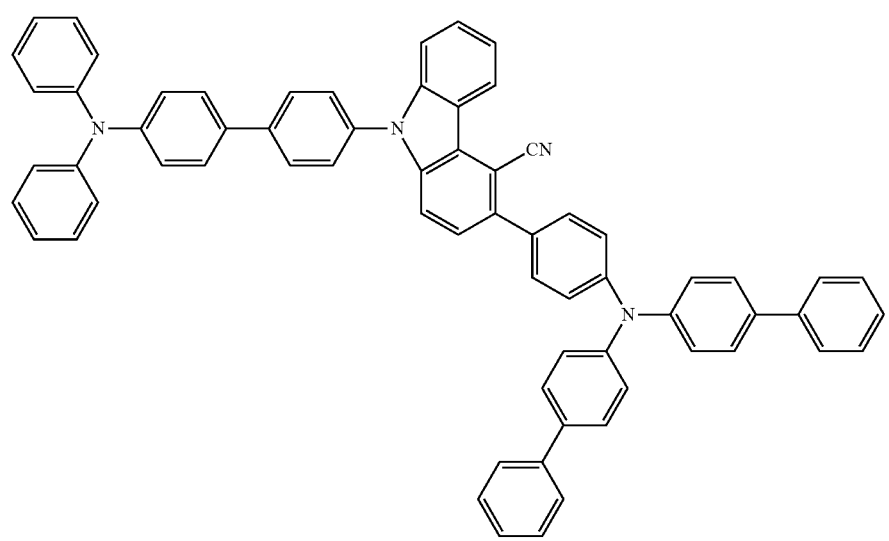
[Chemical Formula 32]
(Compound 30)
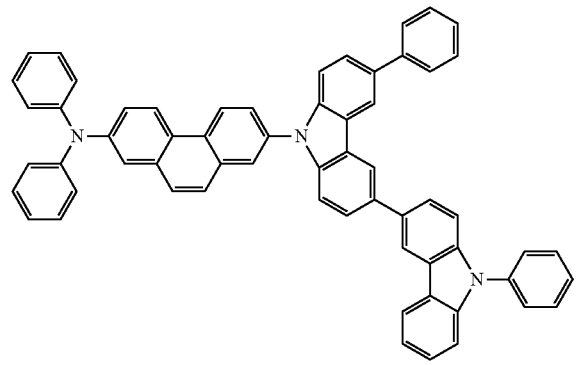
[Chemical Formula 33]
(Compound 31)
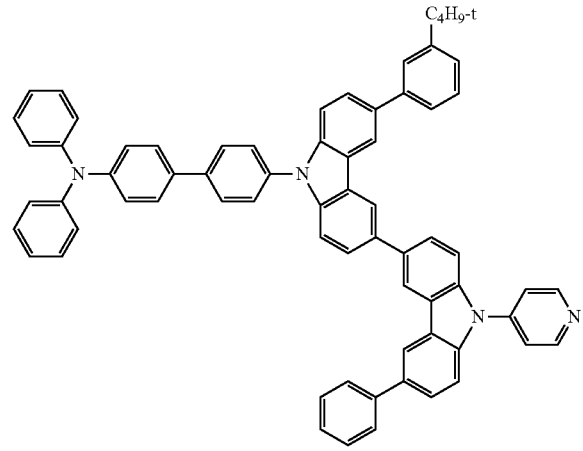

[Chemical Formula 34]
(Compound 32)
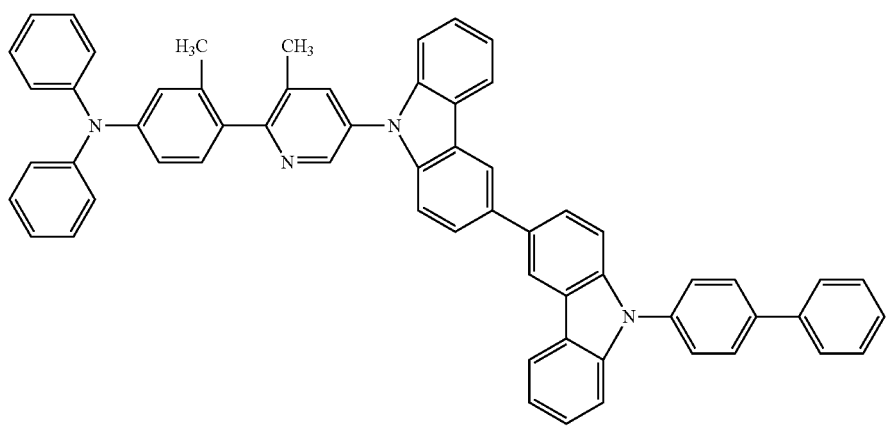
[Chemical Formula 35]
(Compound 33)
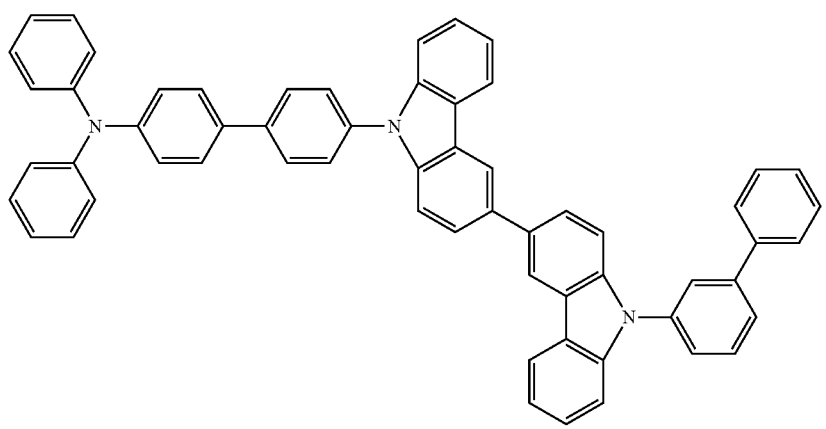
[Chemical Formula 36]
(Compound 34)
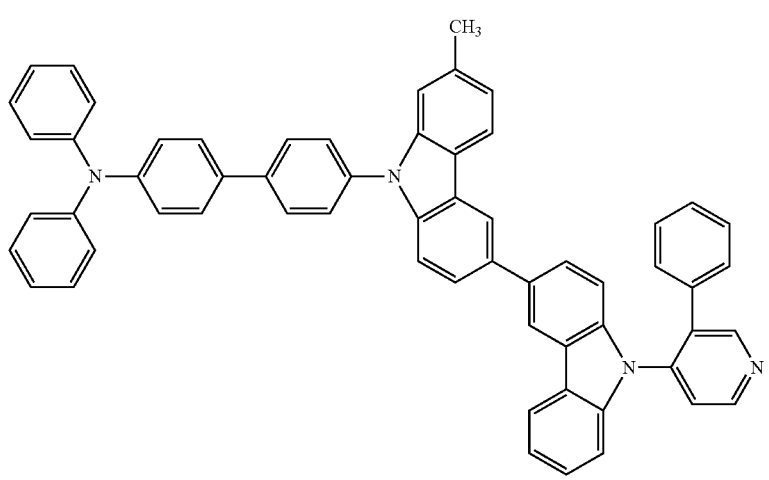

-continued
[Chemical Formula 37]
(Compound 35)
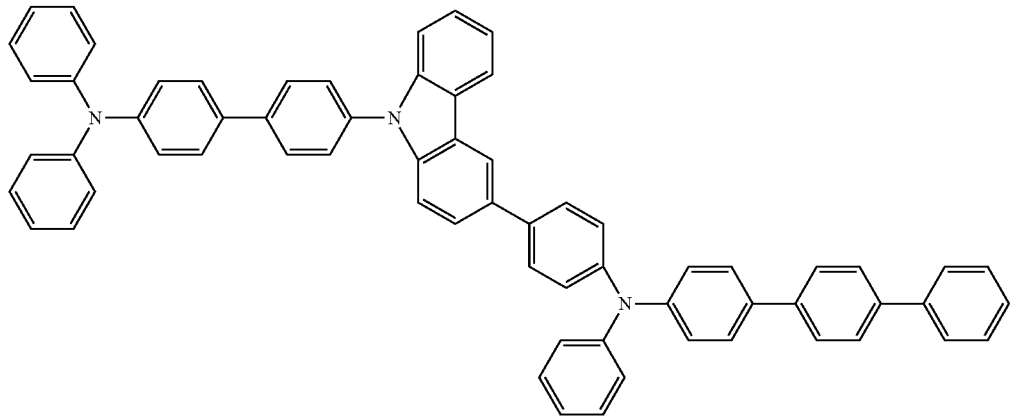
[Chemical Formula 38]
(Compound 36)
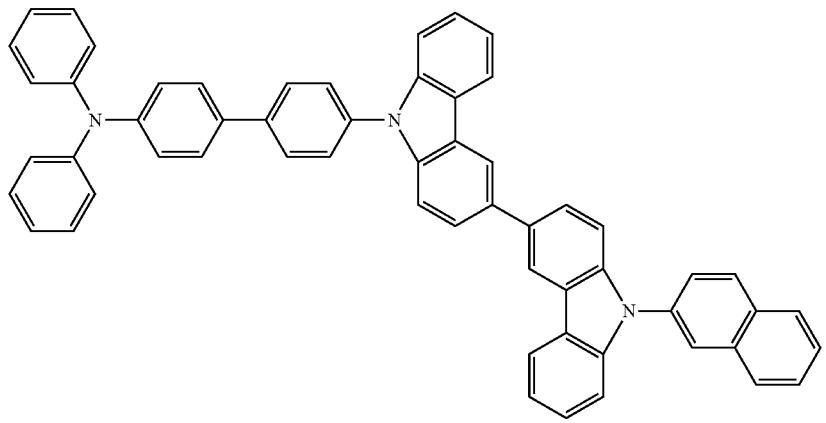
[Chemical Formula 39]
(Compound 37)
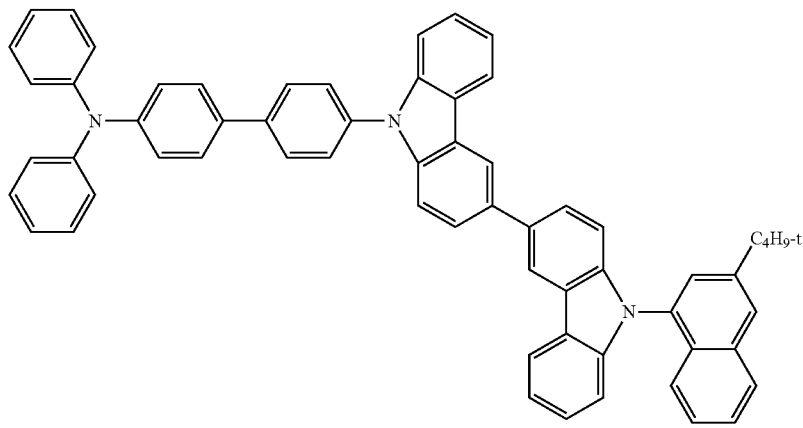

[Chemical Formula 40]
(Compound 38)
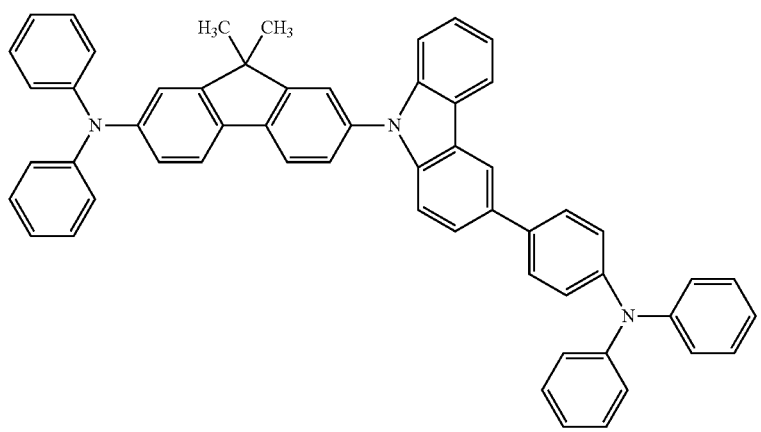
[Chemical Formula 41]
(Compound 39)
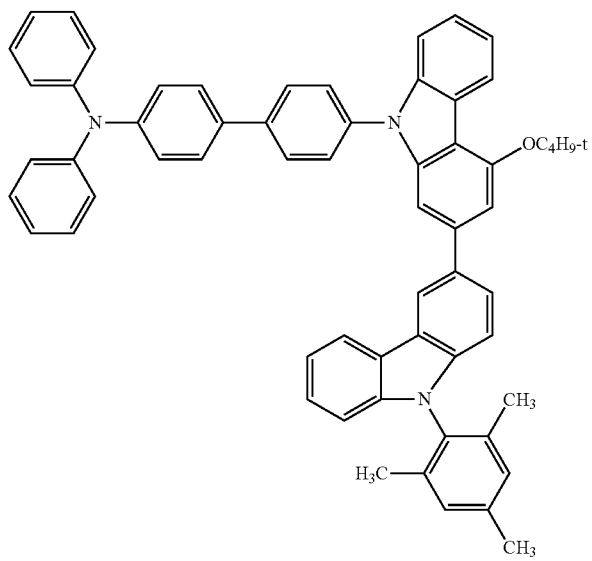
[Chemical Formula 42]
(Compound 40)
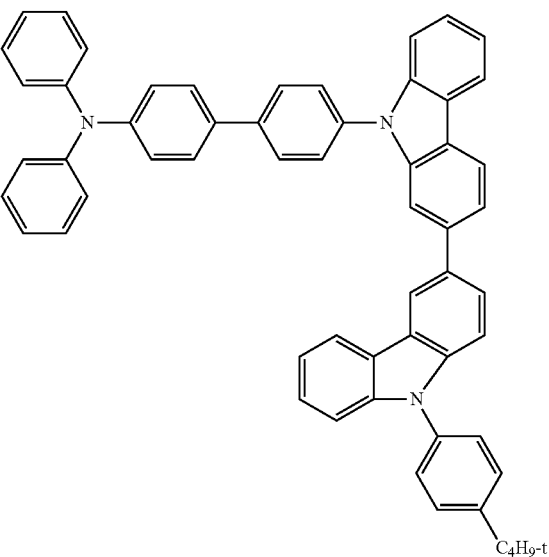

[Chemical Formula 43]
(Compound 41)
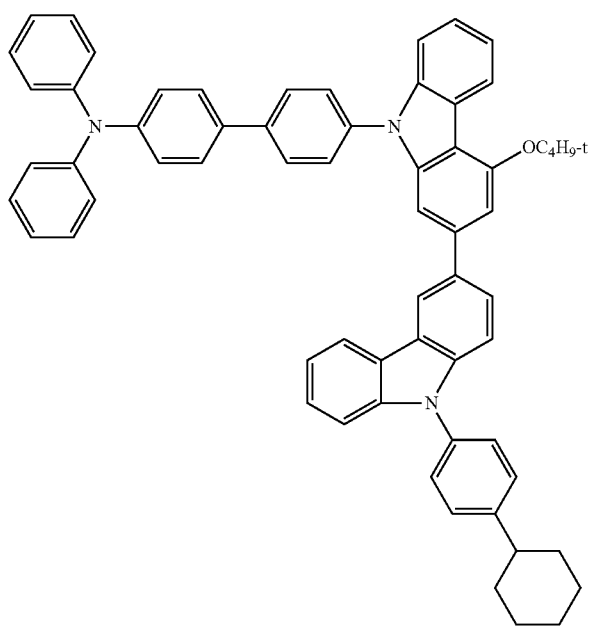
[Chemical Formula 44]
(Compound 42)
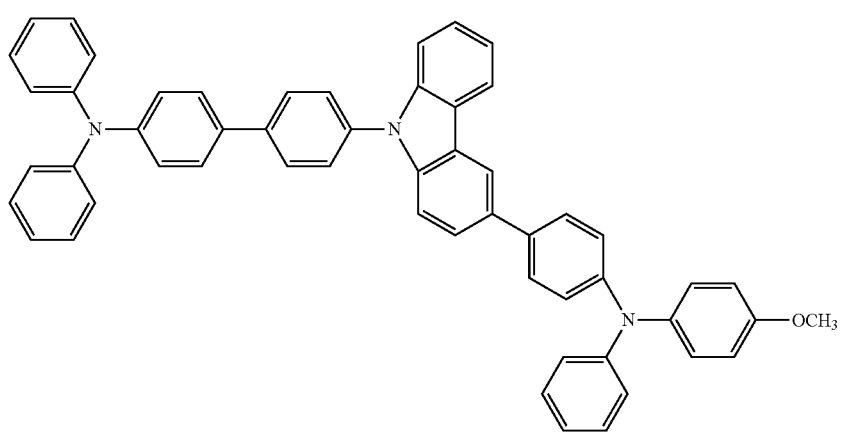
[Chemical Formula 45]
(Compound 43)
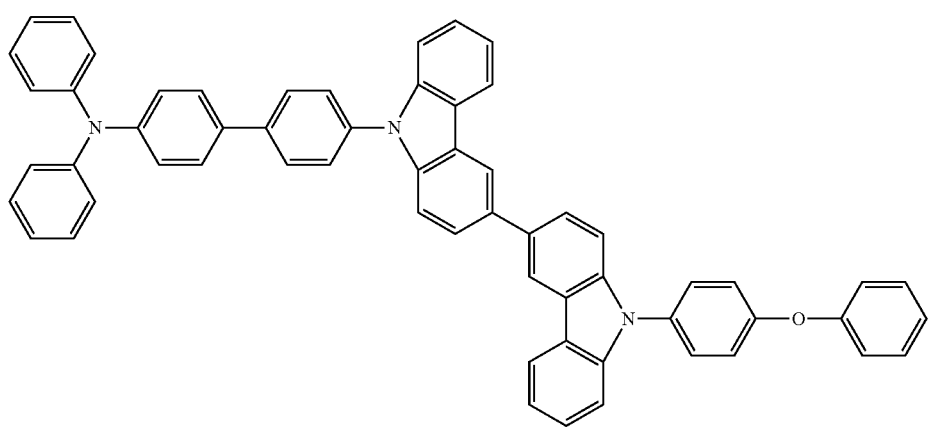

[Chemical Formula 46]
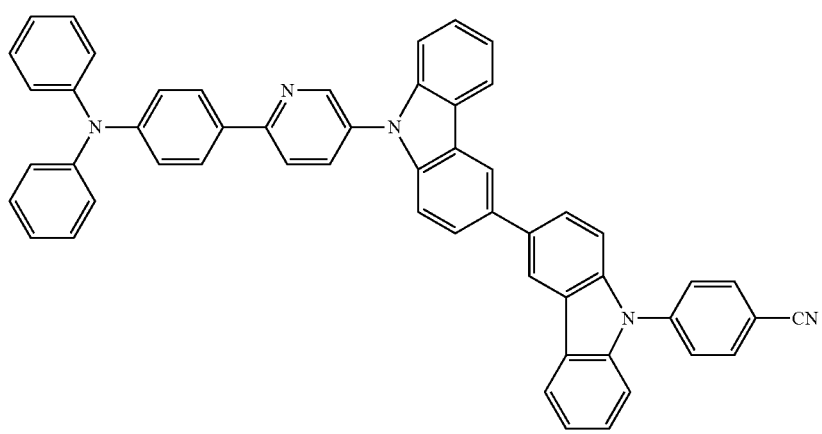
(Compound 44)
[Chemical Formula 47]
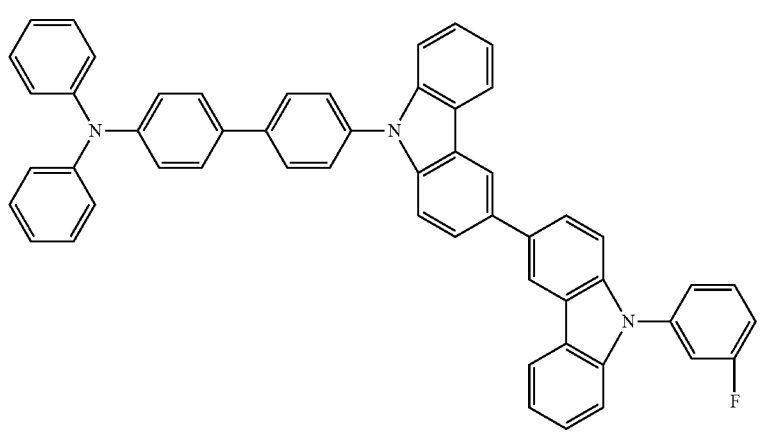
(Compound 45)
[Chemical Formula 48]
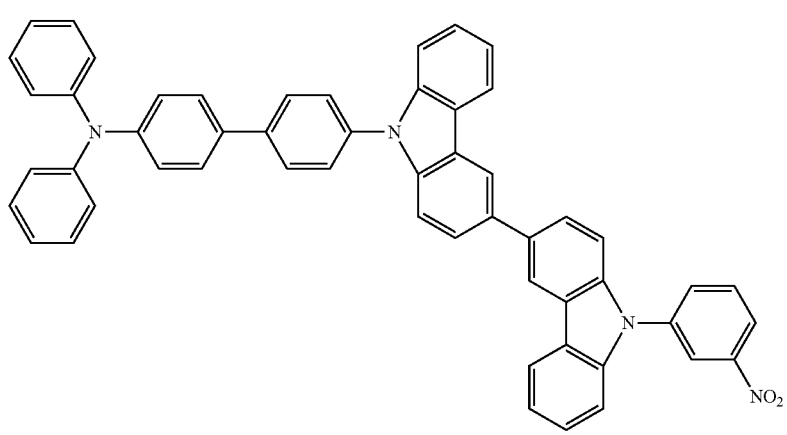
(Compound 46)

-continued
[Chemical Formula 49]
(Compound 47)
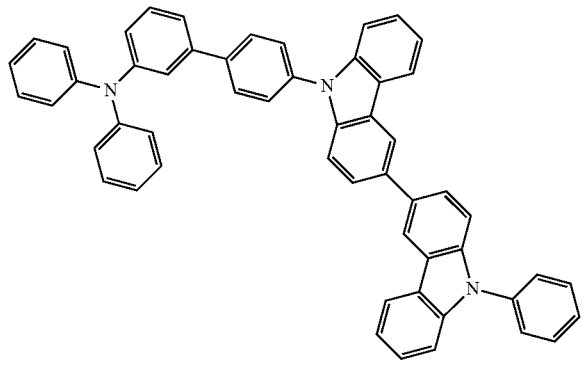
[Chemical Formula 50]
(Compound 48)
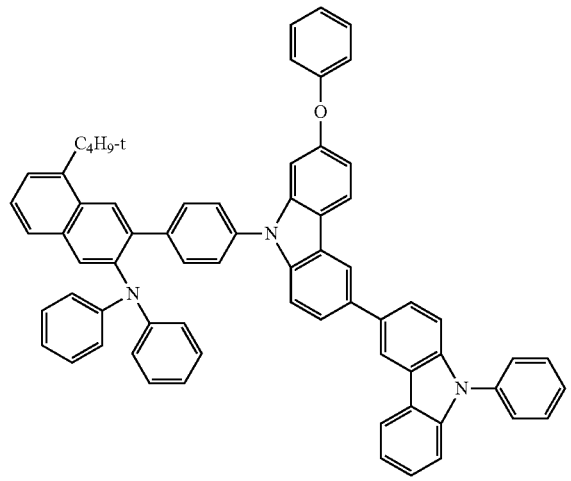
[Chemical Formula 51]
(Compound 49)
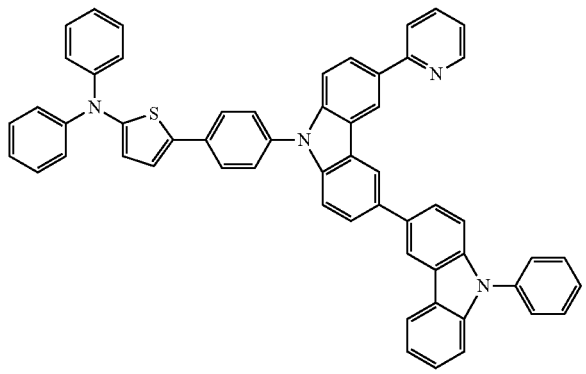
[Chemical Formula 52]
(Compound 50)
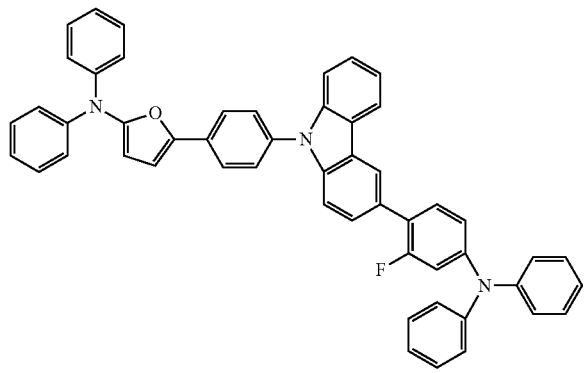
[Chemical Formula 53]
(Compound 51)
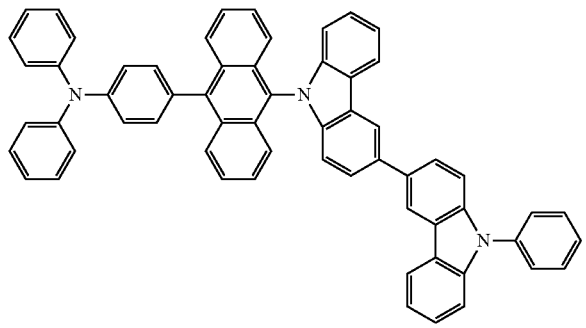
[Chemical Formula 54]
(Compound 52)
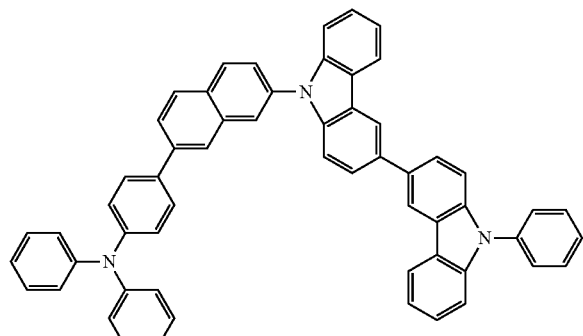

[Chemical Formula 55]
(Compound 53)
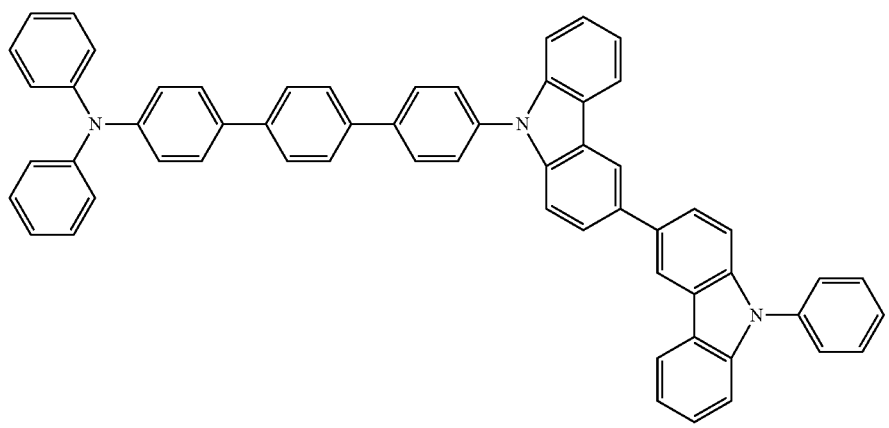
[Chemical Formula 56]
(Compound 54)
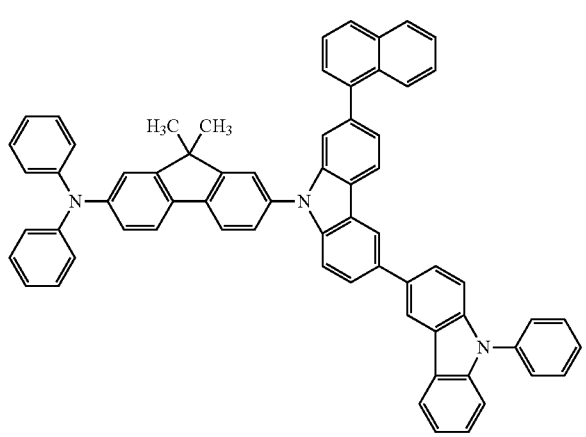
[Chemical Formula 57]
(Compound 55)
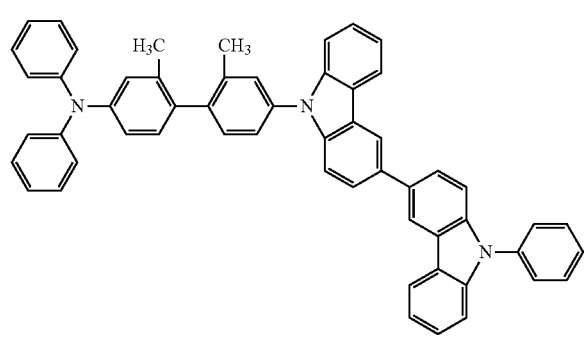
[Chemical Formula 58]
(Compound 56)
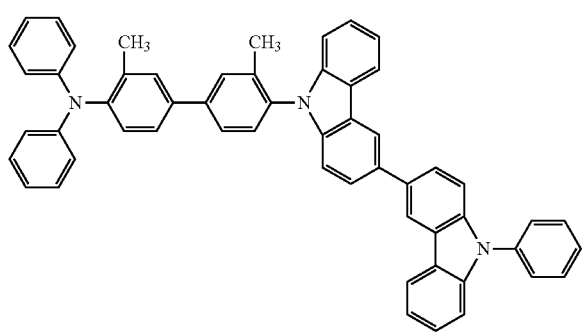
[Chemical Formula 59]
(Compound 57)
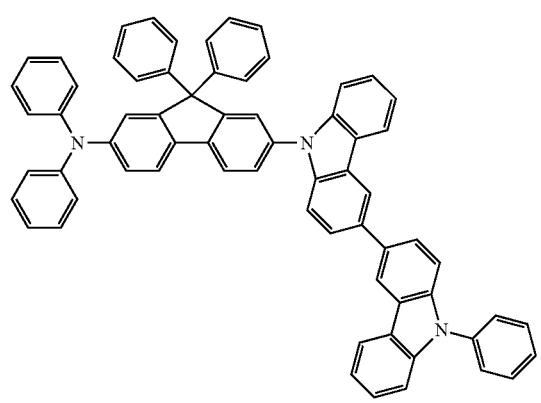

-continued
[Chemical Formula 60]
(Compound 58)
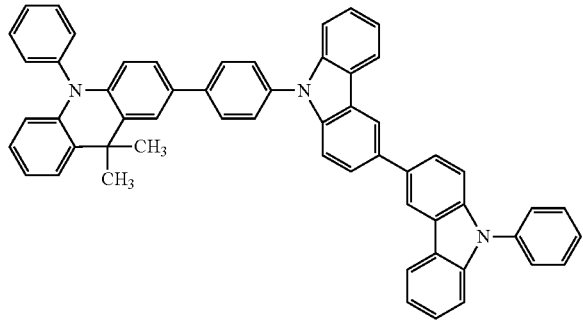
[Chemical Formula 61]
(Compound 59)
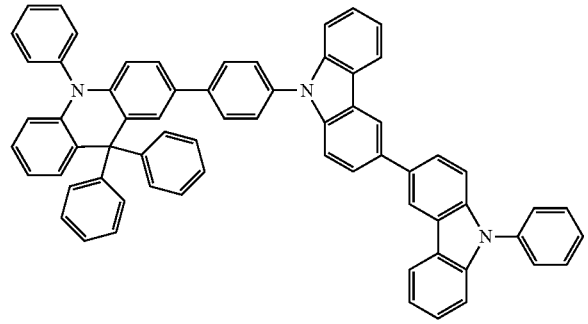
[Chemical Formula 62]
(Compound 60)
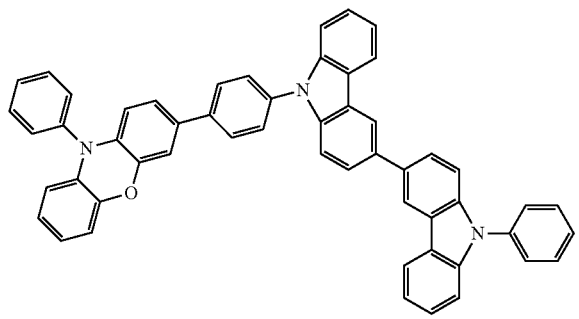
[Chemical Formula 63]
(Compound 61)
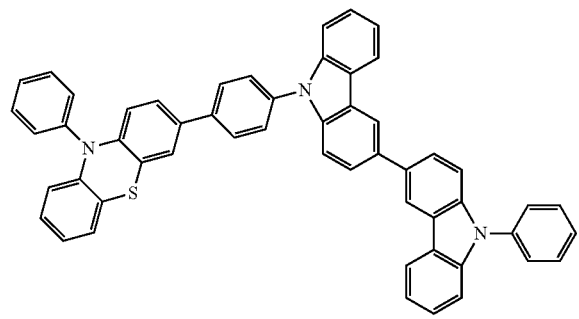
[Chemical Formula 64]
(Compound 62)
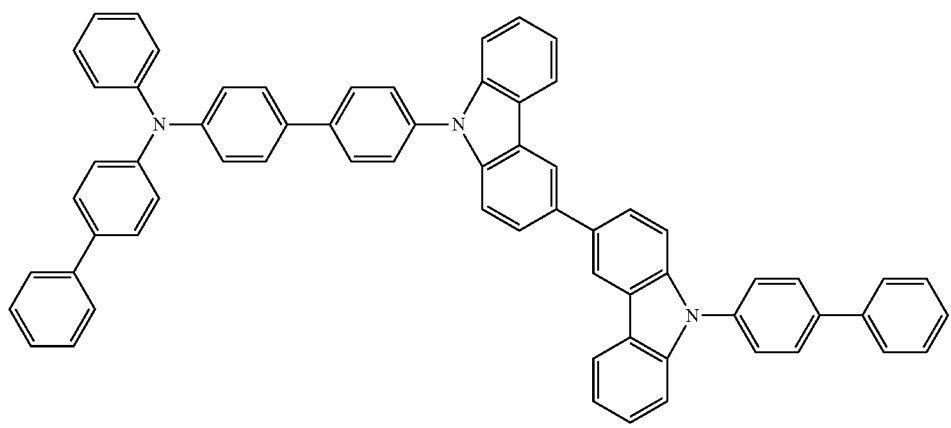

[Chemical Formula 65]
(Compound 63)
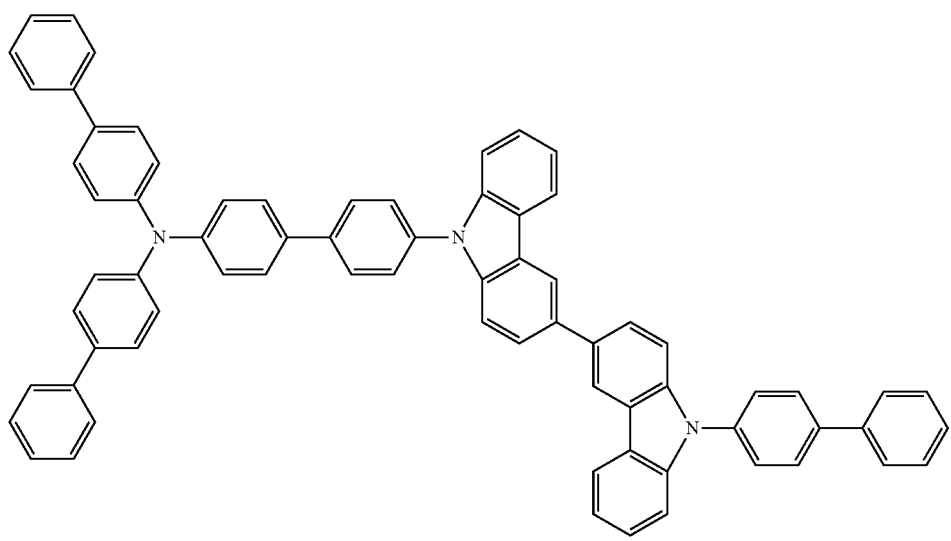
[Chemical Formula 66]
(Compound 64)
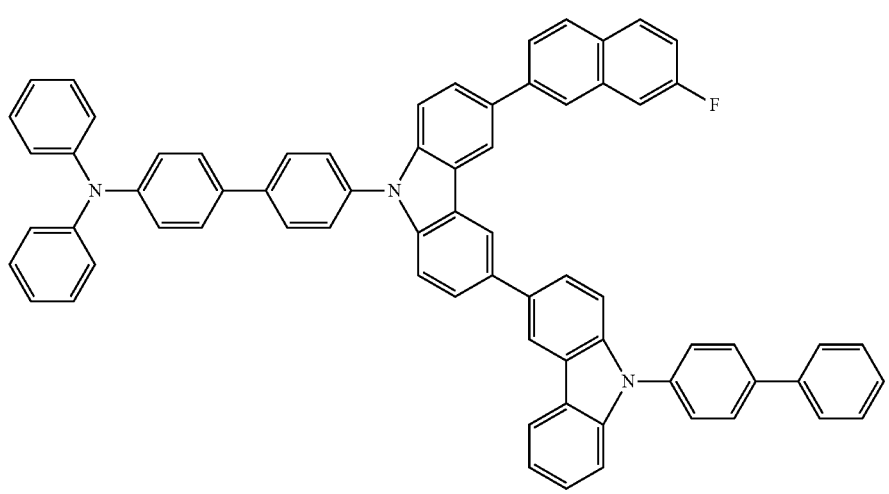
[Chemical Formula 67]
(Compound 65)
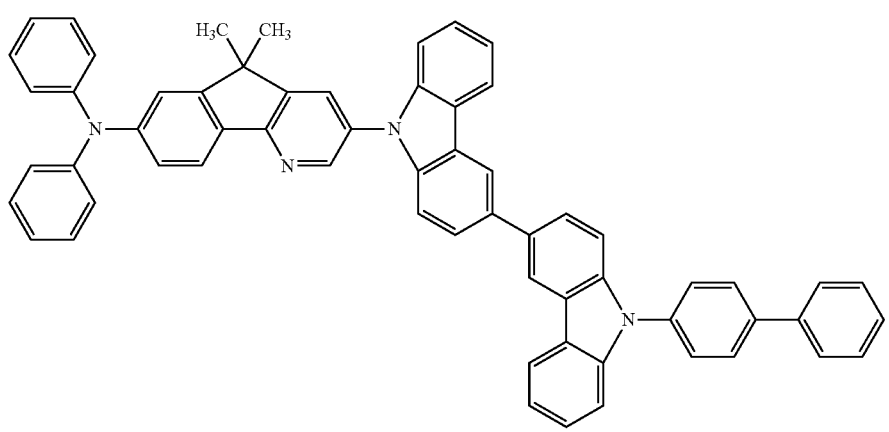

-continued
[Chemical Formula 68]
(Compound 66)
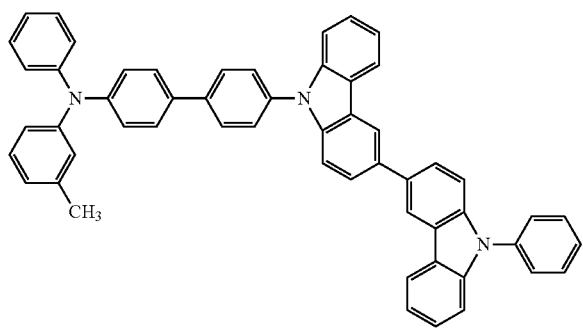
[Chemical Formula 69]
(Compound 67)
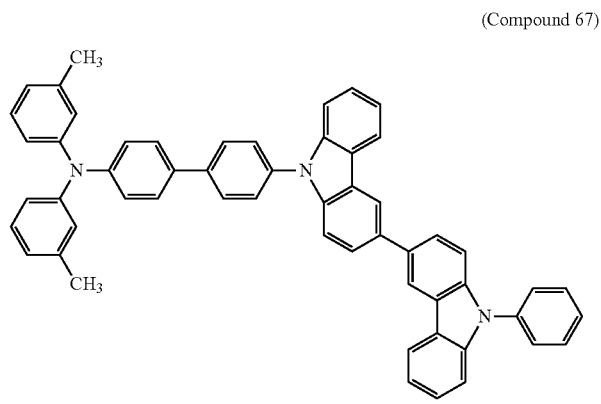
[Chemical Formula 70]
(Compound 68)
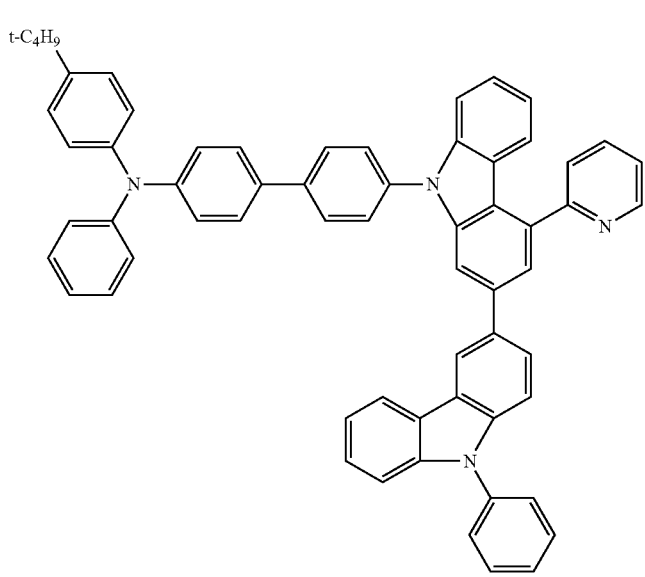
[Chemical Formula 71]
(Compound 69)
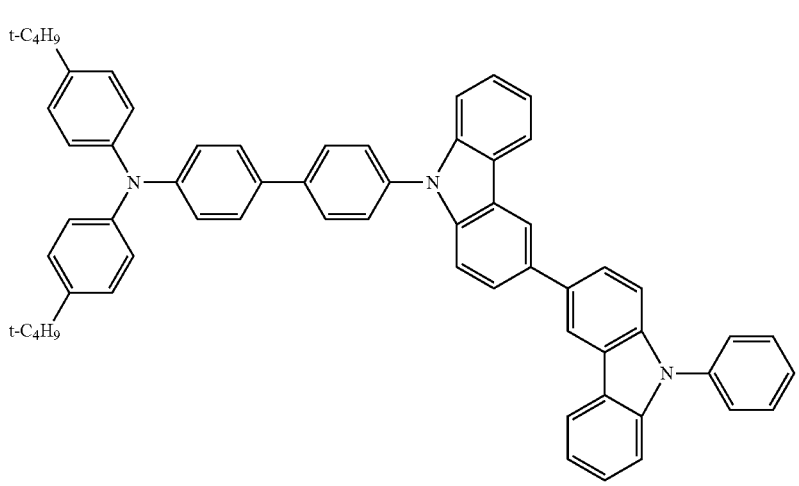

[Chemical Formula 72]
(Compound 70)
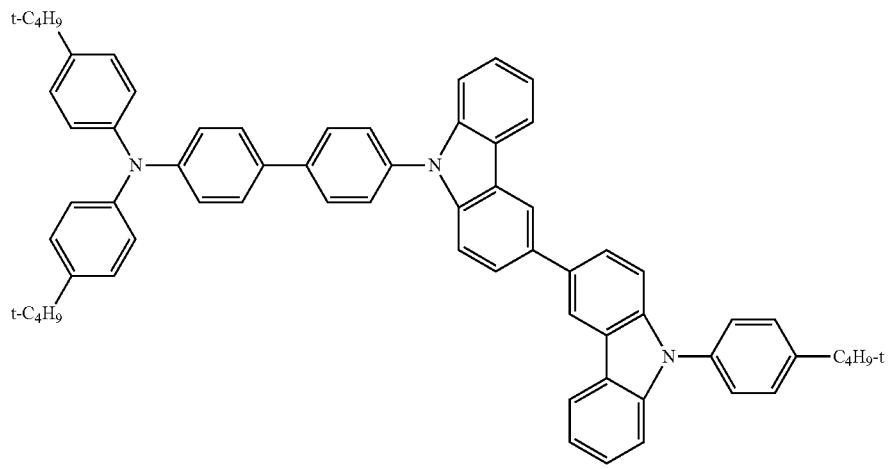
[Chemical Formula 73]
(Compound 71)
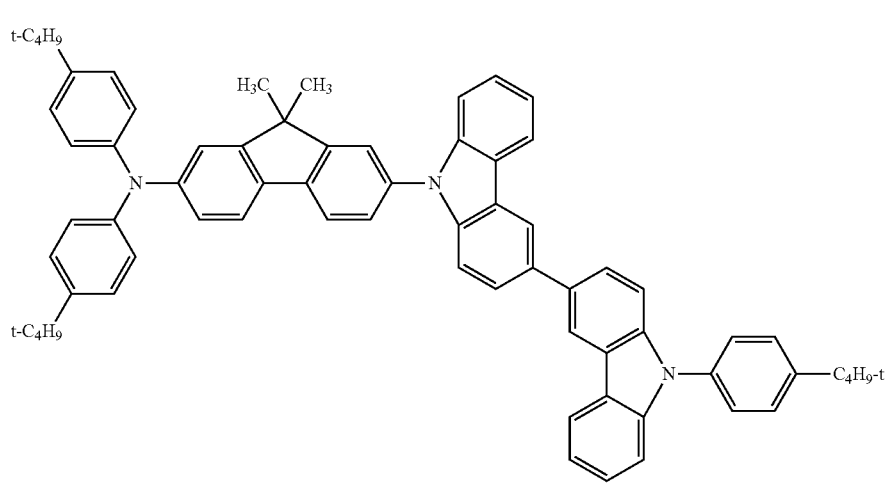
[Chemical Formula 74]
(Compound 72)
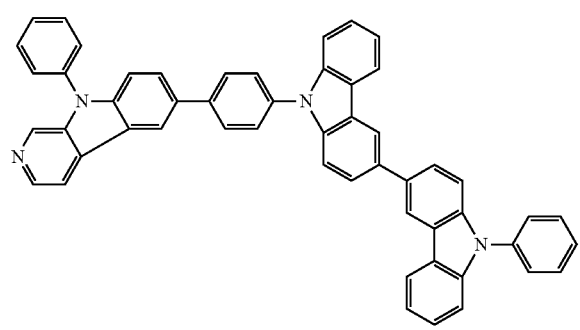
[Chemical Formula 75]
(Compound 73)
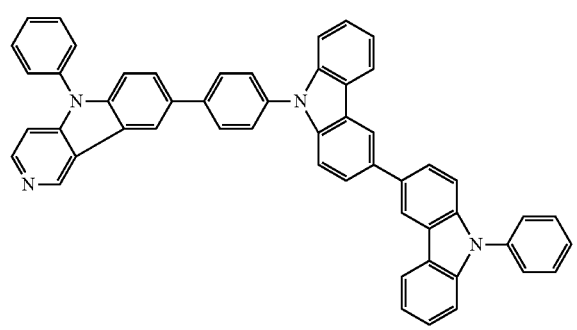

[Chemical Formula 76]
(Compound 74)
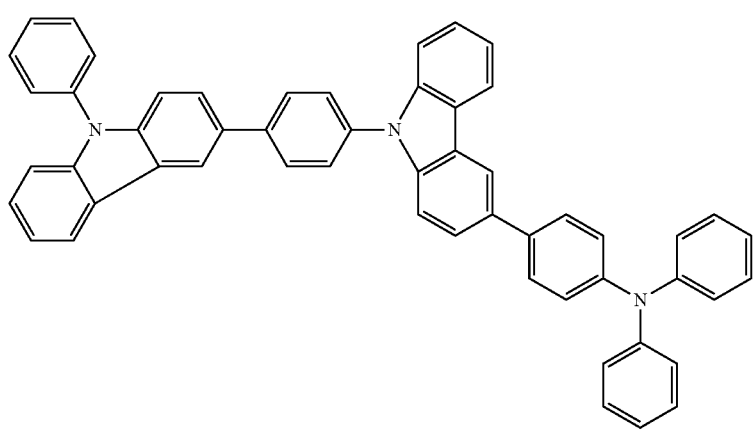
[Chemical Formula 77]
(Compound 75)
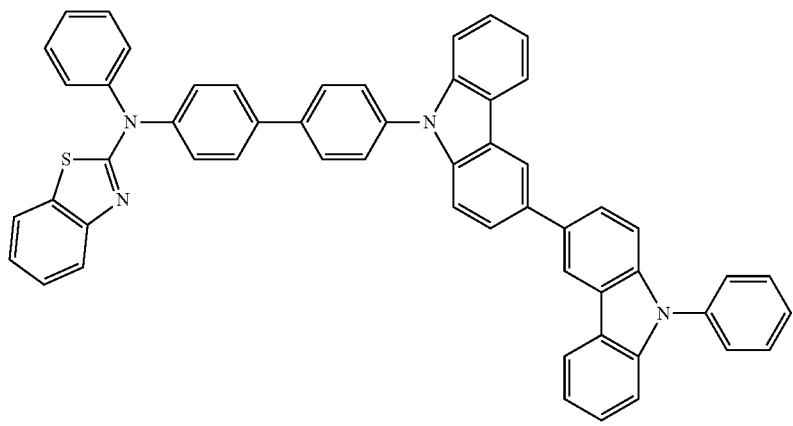
[Chemical Formula 78]
(Compound 76)
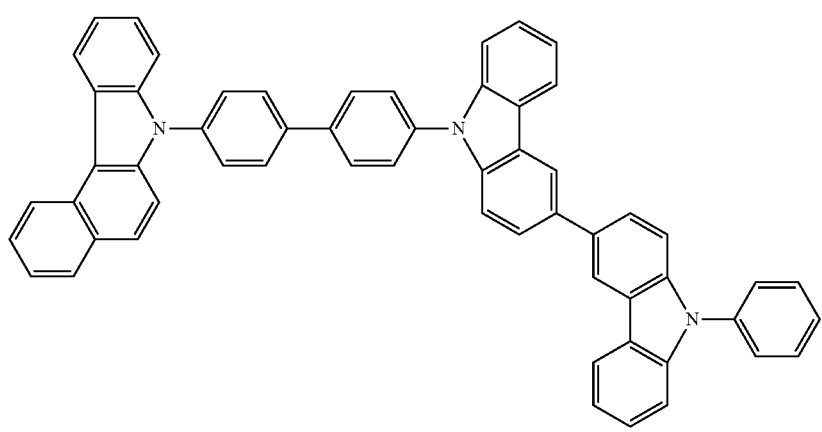

-continued
[Chemical Formula 79]
(Compound 77)
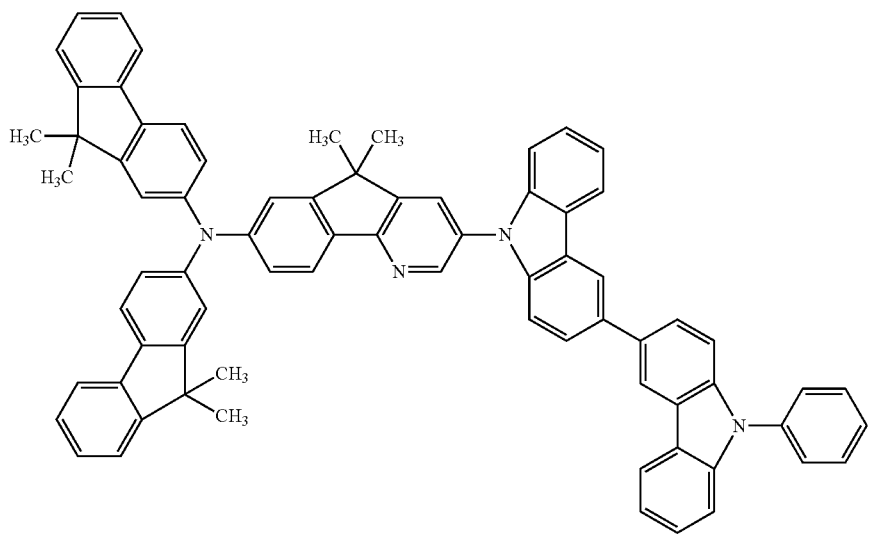
[Chemical Formula 80]
(Compound 78)
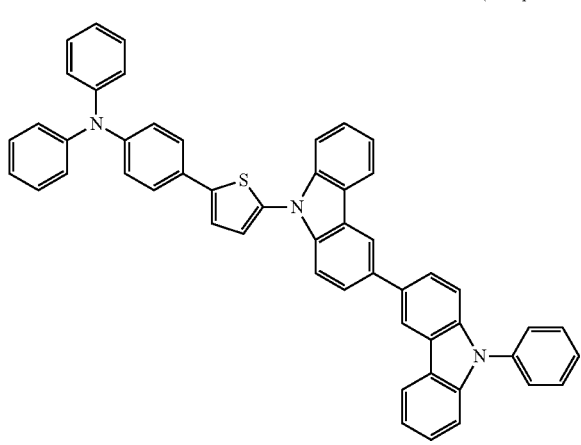
[Chemical Formula 81]
(Compound 79)
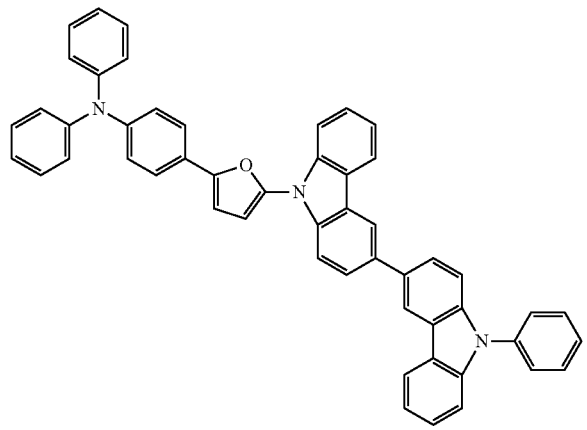
[Chemical Formula 82]
(Compound 80)
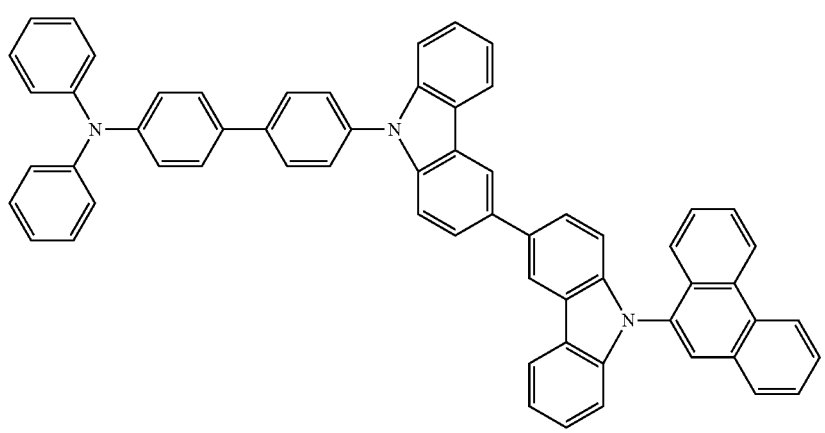

-continued
[Chemical Formula 83]
(Compound 81)
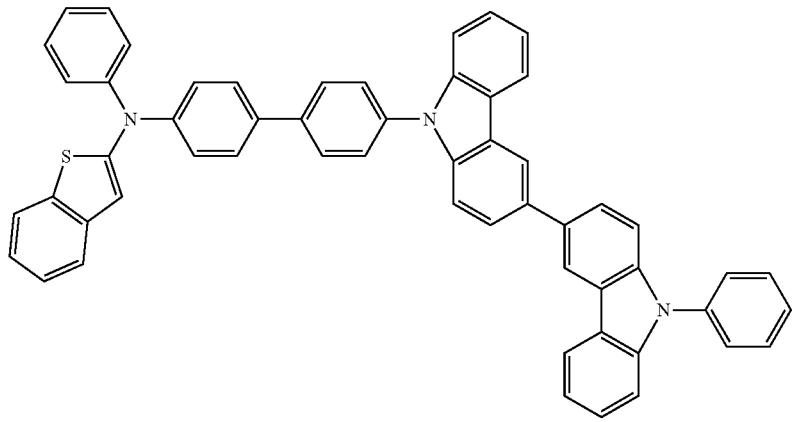
[Chemical Formula 84]
(Compound 82)
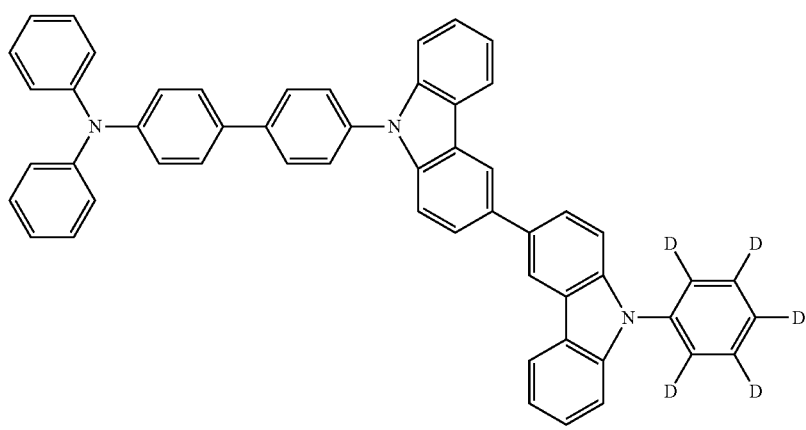
[Chemical Formula 85]
(Compound 83)
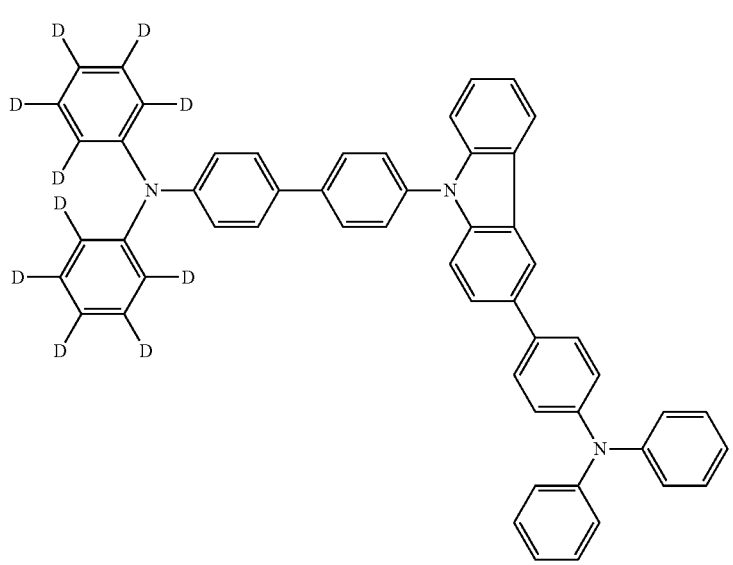

[Chemical Formula 86]

(Compound 84)

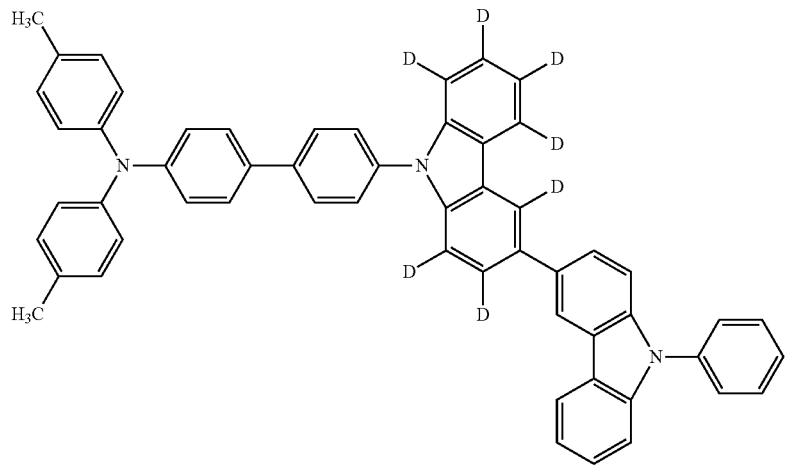

[Chemical Formula 87]

(Compound 85)

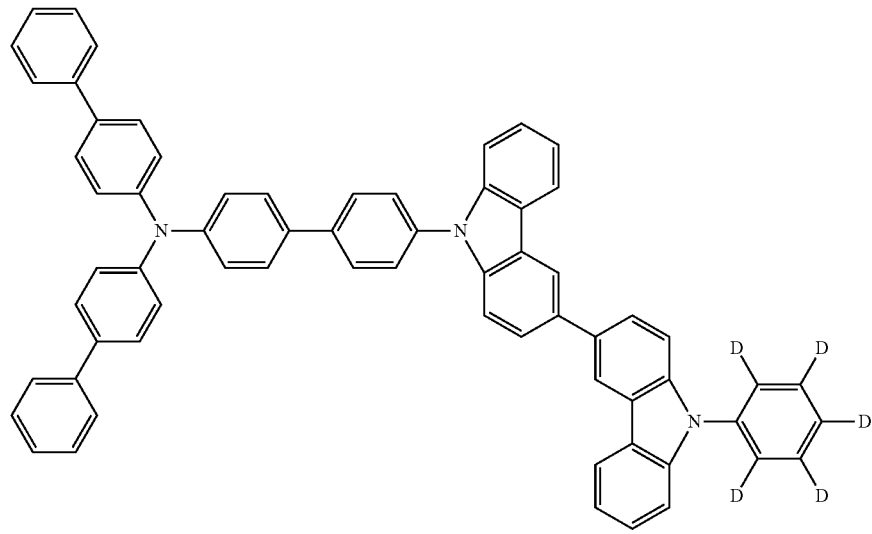

These compounds were purified by methods such as column chromatography, adsorption using, for example, a silica gel, activated carbon, or activated clay, and recrystallization or crystallization using a solvent. The compounds were identified by NMR analysis. Glass transition point (Tg) and work function were taken for the measurement of physical properties. Glass transition point (Tg) can be used as an index of stability in the thin-film state, and the work function as an index of hole transportability.

Glass transition point (Tg) was measured using a powder, using a high-sensitive differential scanning calorimeter (DSC3100S produced by Bruker AXS).

For the measurement of work function, a 100 nm-thick thin film was fabricated on an ITO substrate, and an atmosphere photoelectron spectrometer AC-3 produced by Riken Keiki Co., Ltd. was used.

The organic EL device of the present invention may have a structure including an anode, a hole transport layer, an electron blocking layer, a light emitting layer, an electron transport layer, and a cathode successively formed on a substrate, optionally with a hole injection layer between the anode and the hole transport layer, or with an electron injection layer between the electron transport layer and the cathode. In such multilayer structures, some of the organic layers may be omitted. For example, the device may be configured to include an anode, a hole transport layer, a light emitting layer, an electron transport layer, and a cathode successively formed on a substrate.

Electrode materials with a large work function, such as ITO and gold, are used as the anode of the organic EL device of the present invention. The hole injection layer may be made of material such as porphyrin compounds as represented by copper phthalocyanine, starburst-type triphenylamine derivatives, various triphenylamine tetramers, and coating-type polymer materials, in addition to the compounds of general formula (1) having a carbazole ring structure of the present invention. These materials may be formed into a thin film by using a vapor deposition method, or other known methods such as spin coating and an inkjet method.

Examples of the material used for the hole transport layer of the present invention include benzidine derivatives such as N,N'-diphenyl-N,N'-di(m-tolyl)benzidine (hereinafter, simply "TPD"), N,N'-diphenyl-N,N'-di(α-naphthyl)benzidine (hereinafter, simply "NPD"), and N,N,N',N'-tetrabiphenylylbenzidine, and various triphenylamine trimers and tetramers, in addition to the compounds of general formula (1) having a carbazole ring structure of the present invention. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. Examples of the material used for the hole injection/transport layer include coating-type polymer materials such as poly(3,4-ethylenedioxythiophene) (hereinafter, simply "PEDOT")/poly(styrene sulfonate) (hereinafter, simply "PSS"). These materials may be formed into a thin-film by using a vapor deposition method, or other known methods such as spin coating and an inkjet method.

Examples of the material used for the electron blocking layer of the present invention include compounds having an electron blocking effect, including, for example, carbazole derivatives such as 4,4',4"-tri(N-carbazolyl)triphenylamine (hereinafter, simply "TCTA"), 9,9-bis[4-(carbazol-9-yl) phenyl]fluorene, and 1,3-bis(carbazol-9-yl)benzene (hereinafter, simply "mCP"); and compounds having a triphenylsilyl group and a triarylamine structure, as represented by 9-[4-(carbazol-9-yl)phenyl]-9-[4-(triphenylsilyl)phenyl]-9 H-fluorene, in addition to the compounds of general formula (1) having a carbazole ring structure of the present invention.

Examples of the material used for the light emitting layer of the present invention include various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may be configured from a host material and a dopant material. Examples of the host material include thiazole derivatives, benzimidazole derivatives, and polydialkyl fluorene derivatives, in addition to the foregoing light-emitting materials, and the compounds of general formula (1) having a carbazole ring structure of the present invention. Examples of the dopant material include quinacridone, coumalin, rubrene, perylene, derivatives thereof, benzopyran derivatives, rhodamine derivatives, and aminostyryl derivatives. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Further, the light-emitting materials may be phosphorescent materials. Examples of phosphorescent materials include green phosphorescent materials such as $Ir(ppy)_3$, blue phosphorescent materials such as FIrpic and FIr6, and red phosphorescent materials such as $Btp_2Ir(acac)$. Here, the compounds of general formula (1) having a carbazole ring structure of the present invention may be used as the hole injecting and transporting host material, in addition to carbazole derivatives such as 4,4'-di(N-carbazolyl)biphenyl (hereinafter, simply "CBP"), TCTA, and mCP. Compounds such as 2,2',2"-(1,3,5-phenylene)-tris(1-phenyl-1H-benzimidazole) (hereinafter, simply "TPBI") may be used as the electron transporting host material to produce a high-performance organic EL device.

Examples of the hole blocking layer of the present invention include various rare earth complexes, triazole derivatives, triazine derivatives, and oxadiazole derivatives, in addition to phenanthroline derivatives (such as bathocuproin (hereinafter, simply "BCP")), and quinolinol derivative metal complexes. These materials may also be used as the material of the electron transport layer.

Examples of the electron transport layer of the present invention include various metal complexes, triazole derivatives, triazine derivatives, oxadiazole derivatives, thiadiazole derivatives, carbodiimide derivatives, quinoxaline, derivatives, phenanthroline derivatives, and silole derivatives, in addition to quinolinol derivative metal complexes such as $Alq_3$. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the electron injection layer of the present invention include alkali metal salts such as lithium fluoride, and cesium fluoride, alkali-earth metal salts such as magnesium fluoride, and metal oxides such as aluminum oxide.

The cathode of the present invention may be made of electrode materials having a low work function (such as aluminum), or alloys of electrode materials having an even lower work function (such as a magnesium-silver alloy, a magnesium-indium alloy, and an aluminum-magnesium alloy).

The following describes an embodiment of the present invention in more detail based on Examples. The present invention, however, is not restricted to the following Examples.

EXAMPLE 1

Synthesis of diphenyl-[4'-(9'-phenyl-9H,9'H-[3,3'] bicarbazolyl-9-yl)biphenyl-4-yl]amine (Compound 8)

3-Bromo-9H-carbazole (3.6 g), 9-phenyl-3-(4,4,5,5-tetramethyl-[1,3,2]dioxabororan-2-yl)-9H-carbazole (6.0 g), toluene (40 ml), ethanol (10 ml), and a 2M potassium carbonate aqueous solution (11 ml) were added to a nitrogen-substituted reaction vessel, and aerated with nitrogen gas for 30 min under ultrasonic waves. The mixture was heated after adding tetrakis(triphenylphosphine)palladium (0.85 g), and stirred at 74° C. for 3.5 hours. After adding toluene (100 ml), the mixture was heated, and further stirred at 80° C. for 1 hour. The mixture was then cooled to 50° C., and the insolubles were removed by filtration. The filtrate was then concentrated under reduced pressure to obtain a yellowish white crude product. Toluene (300 ml) was added to dissolve the crude product, and the solution was subjected to adsorptive purification with a NH silica gel (16.11 g), and concentrated under reduced pressure to obtain a white powder. The white powder was then purified by being dispersed and washed in ethyl acetate (35 ml) under heat to obtain a white powder of 9-phenyl-9H,9'H-[3,3']bicarbazolyl (1.96 g; yield 32.7%).

9-Phenyl-9H,9'H-[3,3']bicarbazolyl (1.80 g) N-(4'-iodobiphenyl-4-yl)-diphenylamine (1.88 g), sodium bisulfite (0.07 g), a copper powder (0.013 g), 3,5-di(tert-butyl)salicylic acid (0.05 g), potassium carbonate (0.87 g), and dodecylbenzene (20 ml) were added to a nitrogen-substituted reaction vessel, heated, and stirred at 210° C. for 4 hours. The mixture was cooled to 90° C., extracted with toluene (30 ml), concentrated under reduced pressure, and crystallized from n-hexane (20 ml). As a result, a pale yellowish white powder was obtained. The pale yellowish white powder was then purified twice by recrystallization using toluene/methanol to obtain a white powder of diphenyl-[4'-(9'-phenyl-9H,9'H-[3,3']bicarbazolyl-9-yl)biphenyl-4-yl]amine (Compound 8; 2.34 g; yield 76.5%).

The structure of the resulting white powder was identified by NMR. The 1H-NMR measurement result is presented in FIG. 1.

1H-NMR (THF-$d_8$) detected 37 hydrogen signals, as follows. δ(ppm)=8.56(2H), 8.27(2H), 7.91(2H), 7.82(2H), 7.65-7.71(8H), 7.47-7.65(4H), 7.37-7.42(3H), 7.25-7.29 (6H), 7.13-7.17(6H), 7.03(2H).

EXAMPLE 2

Synthesis of biphenyl-4-yl-[4'-(9'-phenyl-9H,9'H-[3,3']bicarbazolyl-9-yl)biphenyl-4-yl]-phenylamine (Compound 13)

9-(4-Bromophenyl)-9'-phenyl-9H,9'H-[3,3']bicarbazolyl (11 g), biphenyl-4-yl-[4-(4,4,5,5-tetramethyl-[1,3,2]dioxabororan-2-yl)phenyl]-phenylamine (9 g), toluene (130 ml), ethanol (30 ml), and a 2M potassium carbonate aqueous solution (30 ml) were added to a nitrogen-substituted reaction vessel, and aerated with nitrogen gas for 30 min under ultrasonic waves. The mixture was heated after adding triphenylphosphine (0.67 g), and stirred at 70° C. for 6 hours. The organic layer was collected after cooling the mixture to room temperature, and washed with saturated brine (100 ml), dehydrated with magnesium sulfate, and concentrated under reduced pressure to obtain a crude product. The crude product was then purified by silica gel column chromatography to obtain a white powder of biphenyl-4-yl-[4'-(9'-phenyl-9H,9'H-[3,3']bicarbazolyl-9-yl)biphenyl-4-yl]-phenylamine (Compound 13; 14.6 g; yield 74%).

Figure 2:
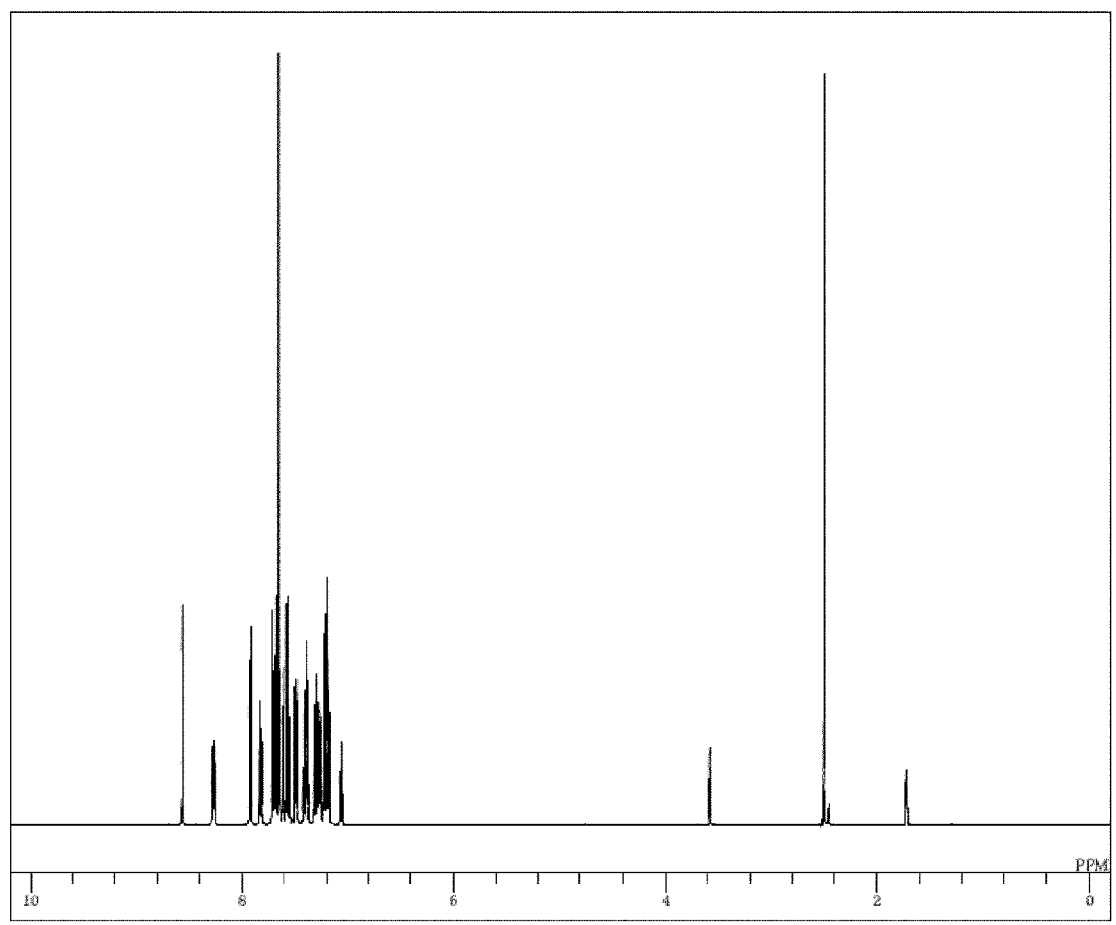
FIG. 2 is a 1H-NMR chart of the compound of Example 2 of the present invention (Compound 13).

The structure of the resulting white powder was identified by NMR. The 1H-NMR measurement result is presented in FIG. 2.

1H-NMR (THF-$d_8$) detected 41 hydrogen signals, as follows. δ(ppm)=8.57(2H), 8.27(2H), 7.92(2H), 7.83(2H), 7.18-7.72(32H), 7.06(1H).

EXAMPLE 3

Synthesis of bis(biphenyl-4-yl)-[4'-(9'-phenyl-9H,9'H-[3,3']bicarbazolyl-9-yl)biphenyl-4-yl]amine (Compound 14)

9-(4-Bromophenyl)-9'-phenyl-9H,9'H-[3,3']bicarbazolyl (11 g), bis(biphenyl-4-yl)-[4-(4,4,5,5-tetramethyl-[1,3,2]dioxabororan-2-yl)phenyl]amine (12 g), toluene (140 ml), ethanol (35 ml), and a 2M potassium carbonate aqueous solution (29 ml) were added to a nitrogen-substituted reaction vessel, and aerated with nitrogen gas for 30 min under ultrasonic waves. The mixture was heated after adding triphenylphosphine (0.68 g), and stirred at 70° C. for 8 hours. The organic layer was collected after cooling the mixture to room temperature, washed with saturated brine (150 ml), dehydrated with magnesium sulfate, and concentrated under reduced pressure to obtain a crude product. The crude product was then purified by silica gel column chromatography to obtain a white powder of bis(biphenyl-4-yl)-[4'-(9'-phenyl-9H,9'H-[3,3']bicarbazolyl-9-yl)biphenyl-4-yl]amine (Compound 14; 12.2 g; yield 71%).

Figure 3:
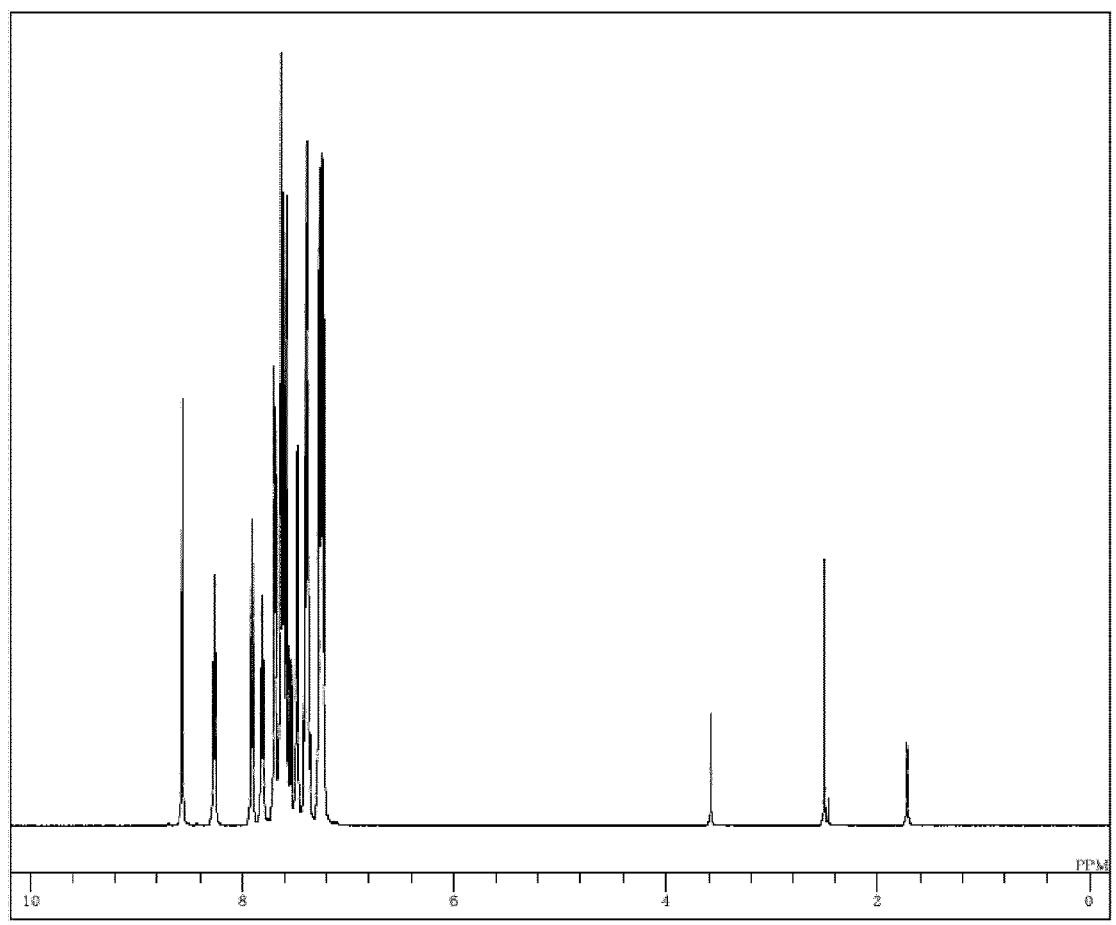
FIG. 3 is a 1H-NMR chart of the compound of Example 3 of the present invention (Compound 14).

The structure of the resulting white powder was identified by NMR. The 1H-NMR measurement result is presented in FIG. 3.

1H-NMR (THF-$d_8$) detected 45 hydrogen signals, as follows. δ(ppm)=8.57(2H), 8.27(2H), 7.92(2H), 7.82(2H), 7.24-7.63(37H).

EXAMPLE 4

Synthesis of diphenyl-[2-(9'-phenyl-9H,9'H-[3,3']bicarbazolyl-9-yl)9,9-dimethylfluoren-7-yl]amine (Compound 22)

9-Phenyl-9H,9'H-[3,3']bicarbazolyl (1.0 g), N-(2-bromo-9,9-dimethylfluoren-7-yl)-diphenylamine (1.08 g), sodium bisulfite (0.04 g), a copper powder (0.008 g), 3,5-di(tert-butyl)salicylic acid (0.031 g), potassium carbonate (0.51 g), and dodecylbenzene (5 ml) were added to a nitrogen-substituted reaction vessel, heated, and stirred at 215° C. for 11 hours. The mixture was cooled to 100° C., extracted with toluene (50 ml), concentrated under reduced pressure, and crystallized from n-hexane (10 ml). As a result, a brown crude crystal was obtained. Toluene (30 ml) was added to dissolve the crude crystal, and the mixture was subjected to adsorptive purification twice using silica gel (8.7 g) to obtain a dark brown crude product. The crude product was dispersed and washed in an ethyl acetate/n-hexane mixed solvent, and then in ethyl acetate, and crystallized with a toluene/methanol mixed solvent to obtain a white powder. The resulting powder was dispersed and washed in ethyl acetate, and then in methanol, and dried under reduced pressure to obtain a white powder of diphenyl-[2-(9'-phenyl-9H,9'H-[3,3']bicarbazolyl-9-yl)9,9-dimethylfluoren-7-yl]amine (Compound 22; 0.87 g; yield 46.3%).

Figure 4:
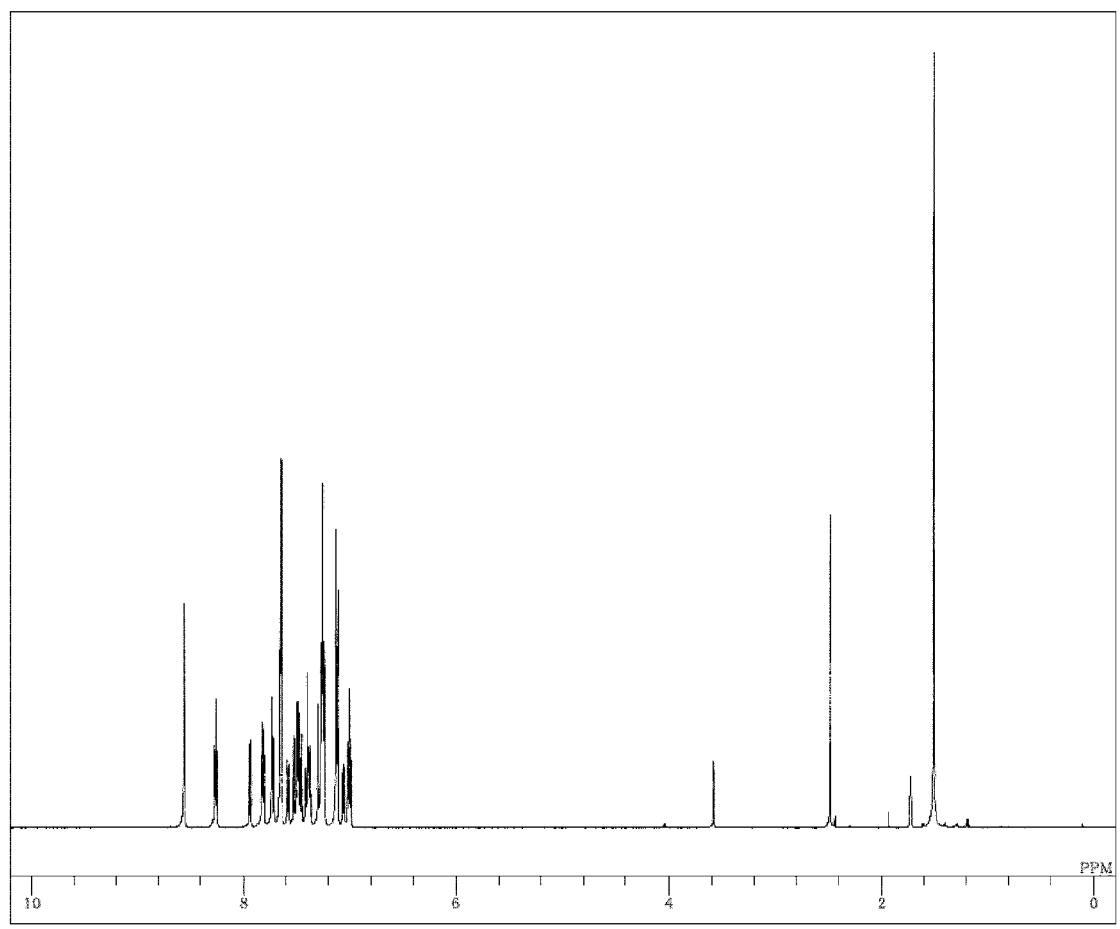
FIG. 4 is a 1H-NMR chart of the compound of Example 4 of the present invention (Compound 22).

The structure of the resulting white powder was identified by NMR. The 1H-NMR measurement result is presented in FIG. 4.

1H-NMR (THF-$d_8$) detected 41 hydrogen signals, as follows. δ(ppm)=8.53(2H), 8.23(2H), 7.90(1H), 7.78(2H), 7.67-7.71(2H), 7.60-7.62(4H), 7.33-7.55(8H), 7.26(1H), 7.20-7.24(6H), 7.10(4H), 6.96-7.03(3H), 1.47(6H).

EXAMPLE 5

Synthesis of diphenyl-[4'-{3-[(diphenylamino)phenyl-4-yl]-9H-carbazolyl-9-yl}biphenyl-4-yl]amine (Compound 26)

3-[(Diphenylamino)phenyl-4-yl]-9H-carbazole (1.5 g), N-(4'-iodo-biphenyl-4-yl)-diphenylamine (1.63 g), sodium bisulfite (0.06 g), a copper powder (0.012 g), 3,5-di(tert-butyl)salicylic acid (0.05 g), potassium carbonate (0.76 g), and dodecylbenzene (10 ml) synthesized in the same manner as in Example 1 were added to a nitrogen-substituted reaction vessel, heated, and stirred at 205° C. for 6.5 hours. The mixture was cooled to 90° C., extracted with toluene (50 ml), concentrated under reduced pressure, and crystallized from n-hexane (30 ml). As a result, a pale yellow crude product was obtained. The crude product was recrystallized with an ethyl acetate/n-hexane mixed solvent, dispersed and washed in ethyl acetate, and then in methanol to obtain a white powder of diphenyl-[4'-{3-[(diphenylamino)phenyl-4-yl]-9H-carbazolyl-9-yl}biphenyl-4-yl]amine (Compound 26; 2.16 g; yield 81.2%).

Figure 5:
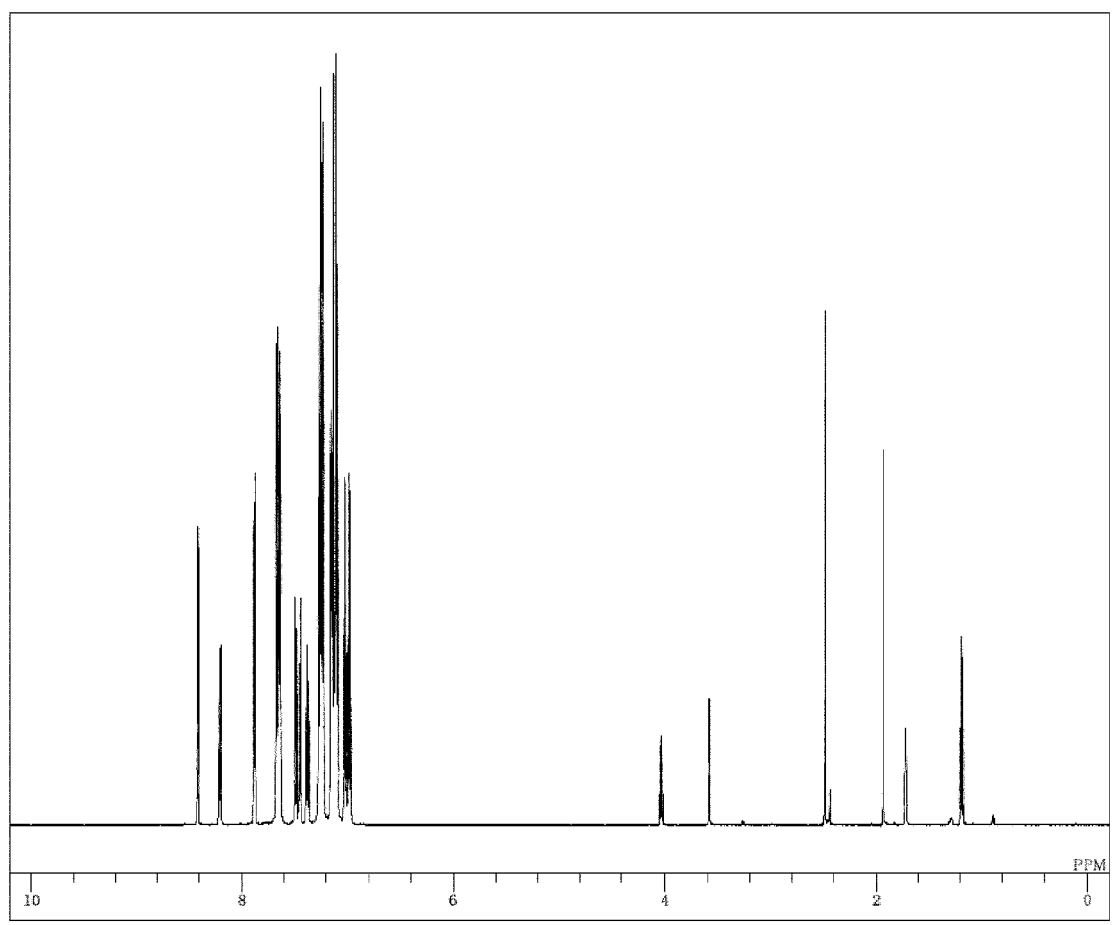
FIG. 5 is a 1H-NMR chart of the compound of Example 5 of the present invention (Compound 26).

The structure of the resulting white powder was identified by NMR. The 1H-NMR measurement result is presented in FIG. 5.

1H-NMR (THF-d$_8$) detected 39 hydrogen signals, as follows. δ(ppm)=8.43(1H), 8.22(1H), 7.89(2H), 7.64-7.68 (7H), 7.46-7.53(2H), 7.39(1H), 7.24-7.29(9H), 7.11-7.17 (12H), 6.98-7.05(4H)

EXAMPLE 6

Synthesis of diphenyl-[2-{3-[(diphenylamino)phenyl-4-yl]-9H-carbazolyl-9-yl}-9,9-dimethylfluoren-7-yl]amine (Compound 38)

3-[(Diphenylamino)phenyl-4-yl]-9H-carbazole (1.03 g), N-(2-bromo-9,9-dimethylfluoren-7-yl)-diphenylamine (1.1 g), sodium bisulfite (0.04 g), a copper powder (0.008 g), 3,5-di(tert-butyl)salicylic acid (0.031 g), potassium carbonate (0.52 g), and dodecylbenzene (8 ml) synthesized in the same manner as in Example 1 were added to a nitrogen-substituted reaction vessel, heated, and stirred at 210 to 215° C. for 26 hours. The mixture was cooled to 90° C., extracted with toluene (30 ml), and concentrated under reduced pressure to obtain a red brown crude product. The crude product was purified by silica gel column chromatography, crystallized with an ethyl acetate/n-hexane mixed solvent, and dispersed and washed in methanol to obtain a pale yellow powder of diphenyl-[2-{3-[(diphenylamino)phenyl-4-yl]-9H-carbazolyl-9-yl}-9,9-dimethylfluoren-7-yl]amine (Compound 38; 1.49 g; yield 77.6%).

Figure 6:
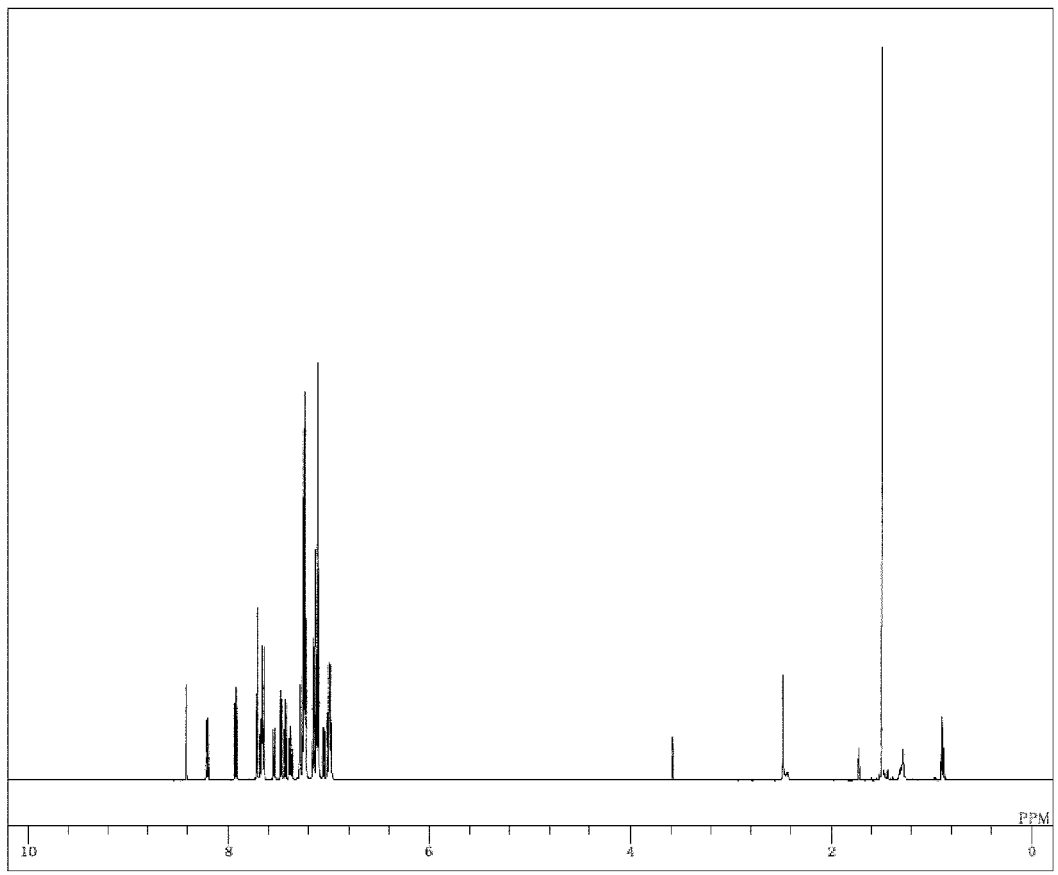
FIG. 6 is a 1H-NMR chart of the compound of Example 6 of the present invention (Compound 38).

The structure of the resulting pale yellow powder was identified by NMR. The 1H-NMR measurement result is presented in FIG. 6.

1H-NMR (THF-d$_8$) detected 43 hydrogen signals, as follows. δ(ppm)=8.43(1H), 8.22(1H), 7.93(1H), 7.65-7.73 (5H), 7.55(1H), 7.48(1H), 7.45(1H), 7.38(1H), 7.23-7.30 (10H), 7.11-7.17(10H), 7.06(1H), 6.98-7.02(4H), 1.50(6H)

EXAMPLE 7

The glass transition points of the compounds of the present invention were determined using a high-sensitive differential scanning calorimeter (DSC 3100S produced by Bruker AXS).

|  | Glass transition point |
| --- | --- |
| Compound of Example 1 of the present invention | 137° C. |
| Compound of Example 2 of the present invention | 144° C. |
| Compound of Example 3 of the present invention | 158° C. |
| Compound of Example 4 of the present invention | 152° C. |
| Compound of Example 5 of the present invention | 126° C. |
| Compound of Example 6 of the present invention | 137° C. |

The compounds of the present invention have glass transition points of 100° C. or higher, demonstrating that the compounds of the present invention have a stable thin-film state.

EXAMPLE 8

A 100 nm-thick vapor-deposited film was fabricated on an ITO substrate using the compounds of the present invention, and the work function was measured using an atmospheric photoelectron spectrometer (Model AC-3 produced by Riken Keiki Co., Ltd.).

|  | Work function |
| --- | --- |
| Compound of Example 1 of the present invention | 5.54 eV |
| Compound of Example 2 of the present invention | 5.53 eV |
| Compound of Example 3 of the present invention | 5.54 eV |
| Compound of Example 4 of the present invention | 5.51 eV |
| Compound of Example 5 of the present invention | 5.55 eV |
| Compound of Example 6 of the present invention | 5.53 eV |

As the results show, the compounds of the present invention have desirable energy levels compared to the work function 5.4 eV of common hole transport materials such as NPD and TPD, and thus possess desirable hole transportability.

EXAMPLE 9

Figure 7:
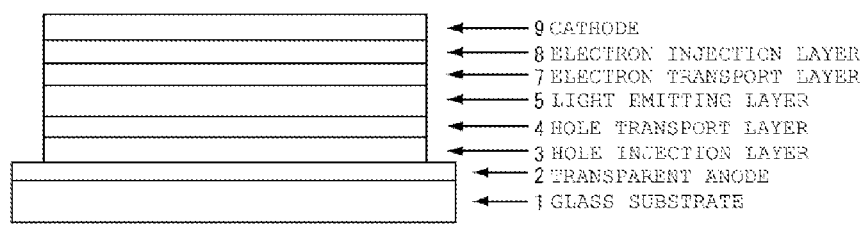
FIG. 7 is a diagram illustrating the configuration of the EL devices of Examples 9 to 12 and Comparative Examples 1 and 2.

The organic EL device, as illustrated in FIG. 7, was fabricated from a hole injection layer 3, a hole transport layer 4, a light emitting layer 5, an electron transport layer 7, an electron injection layer 8, and a cathode (aluminum electrode) 9 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole injection layer 3 by forming Compound 86 of the structural formula below over the transparent anode 2 in a thickness of 20 nm. The hole transport layer 4 was then formed on the hole injection layer 3 by forming the compound of Example 1 of the present invention (Compound 8) in a thickness of 40 nm. Thereafter, the light emitting layer 5 was formed on the hole transport layer 4 by forming Compounds 87 and 88 of the structural formulae below in a thickness of 30 nm using dual vapor deposition at a deposition rate ratio of compound 87:compound 88=5:95. The electron transport layer 7 was then formed on the light emitting layer 5 by forming Alq$_3$ in a thickness of 30 nm. Then, the electron injection layer 8 was formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature.

Table 1 summarizes the results of the emission characteristics measurements performed by applying a DC voltage to the organic EL device fabricated with the compound of Example 1 of the present invention (Compound 8).

[Chemical Formula 88]

(Compound 86)

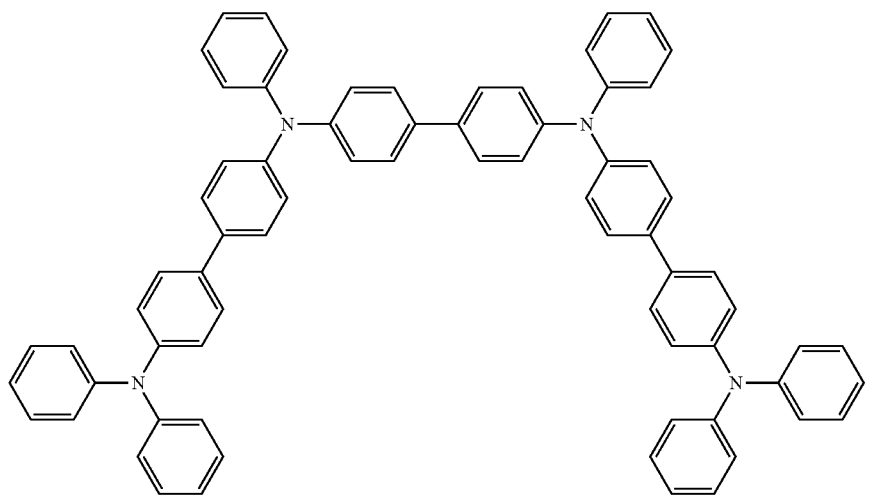

[Chemical Formula 89]

(Compound 87)

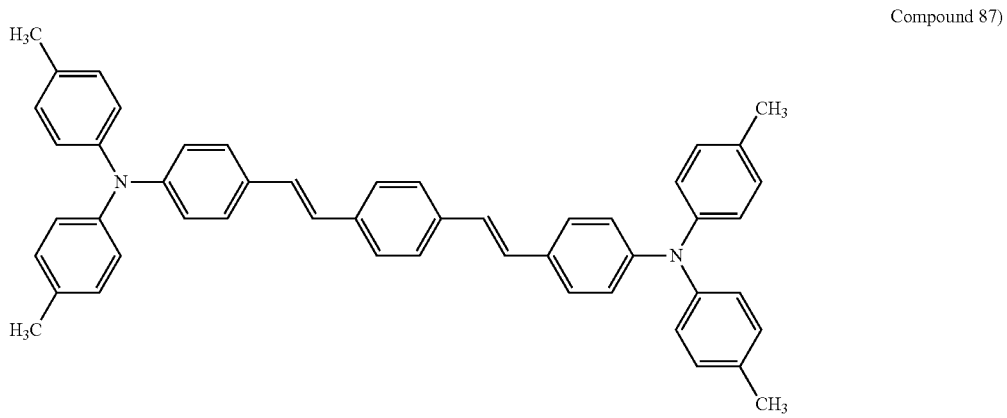

[Chemical Formula 90]

(Compound 88)

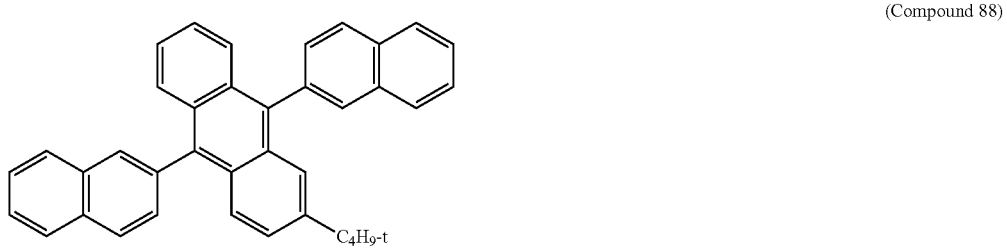

EXAMPLE 10

An organic EL device was fabricated under the same conditions used in Example 9, except that the compound of Example 4 of the present invention (Compound 22) was used as the material of the hole transport layer 4 of Example 9. The characteristics of the organic EL device thus fabricated were measured in an atmosphere at ordinary temperature. Table 1 summarizes the results of the emission characteristics measurements performed by applying a DC voltage to the organic EL device thus fabricated.

EXAMPLE 11

An organic EL device was fabricated under the same conditions used in Example 9, except that the compound of Example 5 of the present invention (Compound 26) was used as the material of the hole transport layer 4 of Example 9. The characteristics of the organic EL device thus fabricated were measured in an atmosphere at ordinary temperature. Table 1 summarizes the results of the emission characteristics measurements performed by applying a DC voltage to the organic EL device thus fabricated.

EXAMPLE 12

An organic EL device was fabricated under the same conditions used in Example 9, except that the compound of Example 6 of the present invention (Compound 38) was used as the material of the hole transport layer 4 of Example 9. The characteristics of the organic EL device thus fabricated were measured in an atmosphere at ordinary temperature. Table 1 summarizes the results of the emission characteristics measurements performed by applying a DC voltage to the organic EL device thus fabricated.

COMPARATIVE EXAMPLE 1

For comparison, an organic EL device was fabricated under the same conditions used in Example 9, except that the Compound B was used as the material of the hole transport layer 4 of Example 9. The characteristics of the organic EL device thus fabricated were measured in an atmosphere at ordinary temperature. Table 1 summarizes the results of the emission characteristics measurements performed by applying a DC voltage to the organic EL device thus fabricated.

COMPARATIVE EXAMPLE 2

For comparison, an organic EL device was fabricated under the same conditions used in Example 9, except that the compound 89 of the following structural formula was used as the material of the hole transport layer 4 of Example 9. The characteristics of the organic EL device thus fabricated were measured in an atmosphere at ordinary temperature. Table 1 summarizes the results of the emission characteristics measurements performed by applying a DC voltage to the organic EL device thus fabricated.

[Chemical Formula 91]

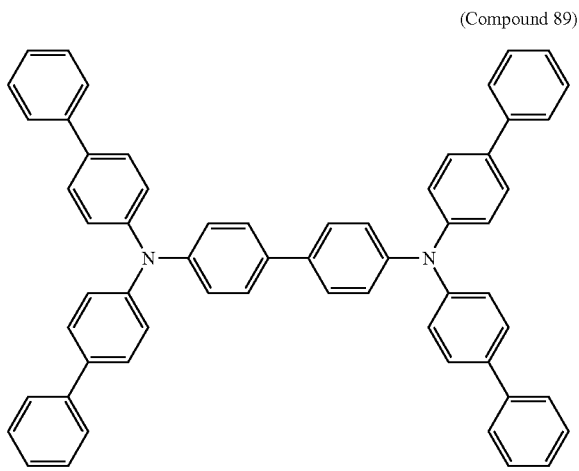

(Compound 89)

TABLE 1

| | Compound | Voltage [V] (@10 mA/cm$^2$) | Luminance [cd/m$^2$] (@10 mA/cm$^2$) | Luminous current efficiency [cd/A] (@10 mA/cm$^2$) | Power efficiency [lm/W] (@10 mA/cm$^2$) |
|---|---|---|---|---|---|
| Ex. 9 | Compound 8 | 4.70 | 805 | 8.06 | 5.39 |
| Ex. 10 | Compound 22 | 4.87 | 993 | 9.94 | 6.41 |
| Ex. 11 | Compound 26 | 5.27 | 954 | 9.55 | 5.69 |
| Ex. 12 | Compound 38 | 5.08 | 1032 | 10.34 | 6.40 |
| Com. Ex. 1 | Compound B | 5.62 | 908 | 9.07 | 5.06 |
| Com. Ex. 2 | Compound 89 | 4.87 | 783 | 7.84 | 5.06 |

As can be seen in Table 1, the driving voltage upon passing a current with a current density of 10 mA/cm$^2$ was 4.70 V with the compound of Example 1 of the present invention (Compound 8), lower than 5.62 V with Compound B and 4.87 V with Compound 89. The compounds of Examples 4 to 6 (Compounds 22, 26, 38) also had lower voltages than Compound B. The compound of Example 1 (Compound 8) of the present invention also had an improved power efficiency of 5.39 lm/W over 5.06 lm/W (Compound B) and 5.06 lm/W (Compound 89). The compounds of Examples 4 to 6 (Compounds 22, 26, 38) had even greater power efficiencies of 5.69 to 6.41 lm/W.

As these results clearly demonstrate, the organic EL devices using the compounds having a carbazole ring structure of the present invention can have improved power efficiency and lower actual driving voltage compared to the organic EL device using the known Compound B.

The results of turn on voltage measurements using the foregoing organic EL devices are presented below.

| Organic EL device | Compound | Turn on voltage [V] |
|---|---|---|
| Example 9 | Compound 8 | 2.7 |
| Comparative Example 1 | Compound B | 2.9 |
| Comparative Example 2 | Compound 89 | 2.8 |

It can be seen that the turn on voltage was lower in Example 9 than in Comparative Examples 1 and 2 in which Compound B and Compound 89 were used, respectively.

EXAMPLE 13

Figure 8:
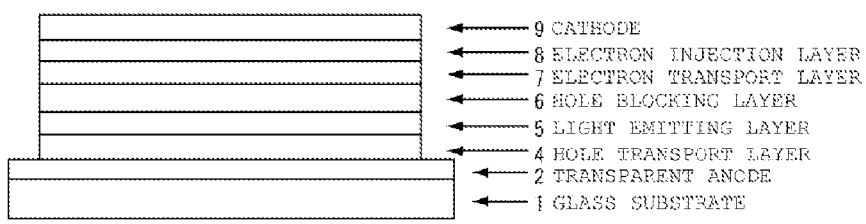
FIG. 8 is a diagram illustrating the configuration of the EL devices of Examples 13 and 14 and Comparative Example 3.

An organic EL device, as illustrated in FIG. 8, was fabricated from a hole transport layer 4, a light emitting layer 5, a hole blocking layer 6, an electron transport layer 7, an electron injection layer 8, and a cathode (aluminum electrode) 9 successively formed by vapor deposition on a glass substrate 1 that had been provided with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole transport layer 4 by forming the compound of Example 1 of the present invention (Compound 8) over the transparent anode 2 in a thickness of 50 nm. Thereafter, the light emitting layer 5 was formed on the hole transport layer 4 by forming TPBI and Ir(ppy)$_3$ in a thickness of 20 nm using dual vapor deposition at a deposition rate that makes the TPBI:Ir(ppy)$_3$ composition ratio 92:8. The hole blocking layer 6 was then formed on the light emitting layer 5 by forming BCP in a thickness of 10 nm. This was followed by formation of the electron transport layer 7 by forming Alq$_3$ on the hole blocking layer 6 in a thickness of 30 nm. Then, the electron injection layer 8 was formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature.

Table 2 summarizes the results of the emission characteristics measurements performed by passing a current of a 10 mA/cm$^2$ current density through the organic EL device fabricated with the compound 8 of Example 1 of the present invention.

EXAMPLE 14

An organic EL device was fabricated under the same conditions used in Example 13, except that the compound of Example 6 of the present invention (Compound 38) was used as the material of the hole transport layer 4 of Example 13. The characteristics of the organic EL device thus fabricated were measured in an atmosphere at ordinary temperature. Table 2 summarizes the results of the emission characteristics measurements performed by applying a DC voltage to the organic EL device thus fabricated.

COMPARATIVE EXAMPLE 3

For comparison, an organic EL device was fabricated under the same conditions used in Example 13, except that the Compound 89 was used as the material of the hole transport layer 4 of Example 13. Table 2 summarizes the results of the emission characteristics measurements performed by passing a current with a current density of 10 mA/cm² through the organic EL device thus fabricated.

TABLE 2

| | Compound | Voltage [V] (@10 mA/cm²) | Luminance [cd/m²] (@10 mA/cm²) | Luminous current efficiency [cd/A] (@10 mA/cm²) | Power efficiency [lm/W] (@10 mA/cm²) |
|---|---|---|---|---|---|
| Ex. 13 | Compound 8 | 5.35 | 3112 | 31.17 | 18.30 |
| Ex. 14 | Compound 38 | 5.30 | 2830 | 28.34 | 16.82 |
| Com. Ex. 3 | Compound 89 | 5.89 | 1896 | 18.98 | 10.13 |

As can be seen in Table 2, the driving voltage upon passing a current with a current density of 10 mA/cm² was 5.35 V with the compound of Example 1 of the present invention (Compound 8), and 5.30 V with the compound of Example 6 (Compound 38), lower than 5.89 V with Compound 89. The compound of Example 1 of the present invention (Compound 8) and the compound of Example 6 (Compound 38) also had greatly improved power efficiencies of 18.30 lm/W and 16.82 lm/W, respectively, over the power efficiency 10.13 lm/W of Compound 89.

As these results clearly demonstrate, the phosphorescent organic EL devices using the compounds having a carbazole ring structure of the present invention can have improved power efficiency and lower actual driving voltage compared to the phosphorescent organic EL device using the known Compound 89.

INDUSTRIAL APPLICABILITY

The compound having a carbazole ring structure of the present invention has good hole transportability, excels in electron blocking ability, and thus has a stable thin-film state. The compound is therefore excellent as a compound for organic EL devices. The organic EL device fabricated with the compound can have high luminous efficiency and high power efficiency, and can have a low actual driving voltage to improve durability. There are potential applications for, for example, home electronic appliances and illuminations.

DESCRIPTION OF REFERENCE NUMERALS AND SIGNS

1 Glass substrate
2 Transparent anode
3 Hole injection layer
4 Hole transport layer
5 Light emitting layer
6 Hole blocking layer
7 Electron transport layer
8 Electron injection layer
9 Cathode

The invention claimed is:
1. A compound of the following general formula (1) having a carbazole ring structure

[Chemical Formula 1]

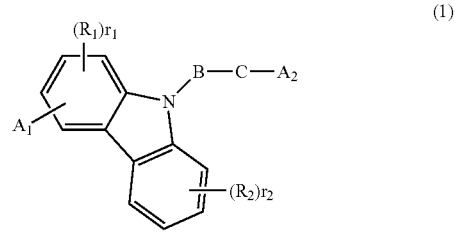

Wherein:
R1 and R2 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, wherein when R2 is a substituted aromatic hydrocarbon, substituted aromatic heterocyclic group, or substituted condensed polycyclic aromatic, the substituent is a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, or phenethyloxy, and wherein r1 represents 0 or an integer of 1 to 3, r2 represents 0 or an integer of 1 to 4;
A1 represents a monovalent group of the general formula (2) below, A2 represents one of the monovalent groups of the general formulae (3) to (7) below;
B represents a divalent group of substituted or unsubstituted aromatic hydrocarbon, a divalent group of a substituted or unsubstituted aromatic heterocyclic ring, or a divalent group of substituted or unsubstituted condensed polycyclic aromatic; and
C represents a single bond, or a divalent group of substituted or unsubstituted aromatic hydrocarbon, a divalent group of a substituted or unsubstituted aromatic heterocyclic ring, or a divalent group of substituted or unsubstituted condensed polycyclic aromatic;

where when B represents a divalent group of substituted or unsubstituted aromatic hydrocarbon, C does not represent a single bond;

[Chemical Formula 2]

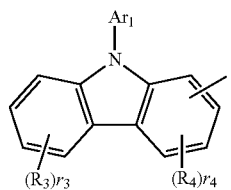

(2)

wherein R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r3 represents 0 or an integer of 1 to 4, r4 represents 0 or an integer of 1 to 3, and Ar1 represents substituted or unsubstituted aromatic hydrocarbon, a substituted or unsubstituted aromatic heterocyclic group, or substituted or unsubstituted condensed polycyclic aromatic, wherein the substituent in the substituted aromatic hydrocarbon, substituted aromatic heterocyclic group, or substituted condensed polycyclic aromatic of Ar1 is a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, and phenethyloxy, wherein the substituent may be further substituted and wherein two or more substituents may bind to each other via a single bond, substituted or unsubstituted methylene, an oxygen atom, or a sulfur atom to form a ring;

[Chemical Formula 3]

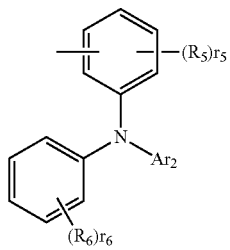

(3)

wherein R5 and R6 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r5 represents 0 or an integer of 1 to 4, r6 represents 0 or an integer of 1 to 5, and Ar2 represents substituted or unsubstituted aromatic hydrocarbon, a substituted or unsubstituted aromatic heterocyclic group, or substituted or unsubstituted condensed polycyclic aromatic;

[Chemical Formula 4]

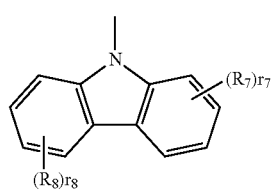

(4)

wherein R7 and R8 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r7 and r8 may be the same or different, and represent 0 or an integer of 1 to 4;

[Chemical Formula 5]

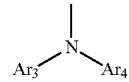

(5)

wherein Ar3 and Ar4 may be the same or different, and represent substituted or unsubstituted aromatic hydrocarbon, a substituted or unsubstituted aromatic heterocyclic group, or substituted or unsubstituted condensed polycyclic aromatic, and these groups may bind to each other via a single bond, substituted or unsubstituted methylene, an oxygen atom, or a sulfur atom to form a ring;

[Chemical Formula 6]

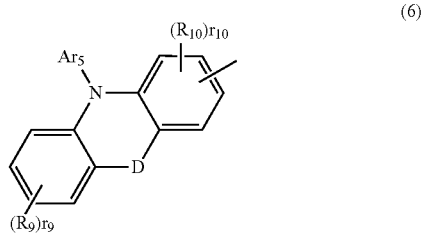

(6)

wherein R9 and R10 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r9 represents 0 or an integer of 1 to 4, r10 represents 0 or an integer of 1 to 3, Ar5 represents substituted or unsubstituted aromatic hydrocarbon, a substituted or unsubstituted aromatic heterocyclic group, or substituted or unsubstituted condensed polycyclic aromatic, and D represents substituted or unsubstituted methylene, an oxygen atom, or a sulfur atom;

[Chemical Formula 7]

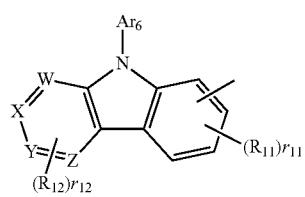

(7)

wherein R11 and R12 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r11 and r12 may be the same or different, and represent 0 or an integer of 1 to 3, Ar6 represents substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom, where only one of W, X, Y, and Z is a nitrogen atom, and, in this case, the nitrogen atom does not have the substituent R12.

2. The compound having a carbazole ring structure according to claim 1, wherein A2 in the general formula (1) is a monovalent group represented by the general formula (3).

3. The compound having a carbazole ring structure according to claim 1, wherein A2 in the general formula (1) is a monovalent group represented by the general formula (4).

4. The compound having a carbazole ring structure according to claim 1, wherein A2 in the general formula (1) is a monovalent group represented by the general formula (5).

5. The compound having a carbazole ring structure according to claim 4, wherein the compound is of the following general formula (1a)

[Chemical Formula 8]

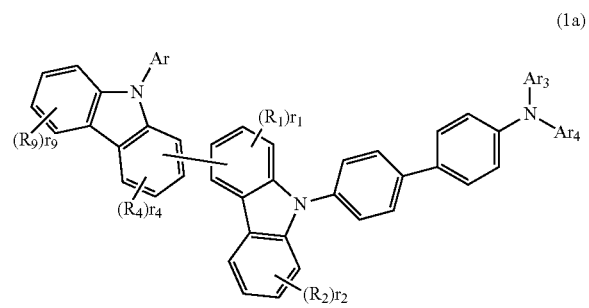

(1a)

wherein R1, R2, R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r1 and r4 may be the same or different, and represent 0 or an integer of 1 to 3, r2 and r3 may be the same or different, and represent 0 or an integer of 1 to 4, and Ar1, Ar3, and Ar4 may be the same or different, and represent substituted or unsubstituted aromatic hydrocarbon, a substituted or unsubstituted aromatic heterocyclic group, or substituted or unsubstituted condensed polycyclic aromatic, where Ar3 and Ar4 may bind to each other via a single bond, substituted or unsubstituted methylene, an oxygen atom, or a sulfur atom to form a ring.

6. The compound having a carbazole ring structure according to claim 4, wherein the compound is of the following general formula (1b)

[Chemical Formula 9]

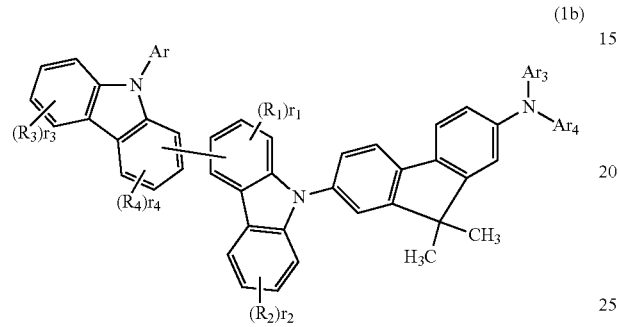

(1b)

wherein R1, R2, R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r1 and r4 may be the same or different, and represent 0 or an integer of 1 to 3, r2 and r3 may be the same or different, and represent 0 or an integer of 1 to 4, and Ar1, Ar3, and Ar4 may be the same or different, and represent substituted or unsubstituted aromatic hydrocarbon, a substituted or unsubstituted aromatic heterocyclic group, or substituted or unsubstituted condensed polycyclic aromatic, where Ar3 and Ar4 may bind to each other via a single bond, substituted or unsubstituted methylene, an oxygen atom, or a sulfur atom to form a ring.

7. An organic electroluminescent device that comprises a pair of electrodes, and one or more organic layers sandwiched between the pair of electrodes,
characterized in that a compound of the following general formula (1) having a carbazole ring structure is used as a constituent material of at least one organic layer

[Chemical Formula 12]

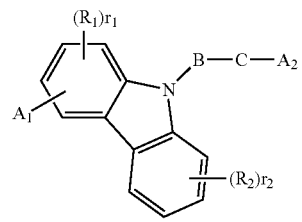

(1)

wherein R1 and R2 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, wherein when R2 is a substituted aromatic hydrocarbon, substituted aromatic heterocyclic group, or substituted condensed polycyclic aromatic, the substituent is a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, or phenethyloxy, and wherein r1 represents 0 or an integer of 1 to 3, r2 represents 0 or an integer of 1 to 4, A1 represents a monovalent group of the general formula (2) below, A2 represents one of the monovalent groups of the general formulae (3) to (7) below, B represents a divalent group of substituted or unsubstituted aromatic hydrocarbon, a divalent group of a substituted or unsubstituted aromatic heterocyclic ring, or a divalent group of substituted or unsubstituted condensed polycyclic aromatic, and C represents a single bond, or a divalent group of substituted or unsubstituted aromatic hydrocarbon, a divalent group of a substituted or unsubstituted aromatic heterocyclic ring, or a divalent group of substituted or unsubstituted condensed polycyclic aromatic, where when B represents a divalent group of substituted or unsubstituted aromatic hydrocarbon, C does not represent a single bond;

[Chemical Formula 13]

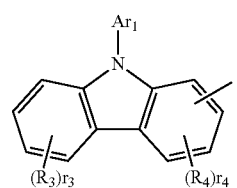

(2)

wherein R3 and R4 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r3 represents 0 or an integer of 1 to 4, r4 represents 0 or an integer of 1 to 3, and Ar1 represents substituted or unsubstituted aromatic hydrocarbon, a substituted or unsubstituted aromatic heterocyclic group, or substituted or unsubstituted condensed polycyclic aromatic, wherein the substituent in the substituted aromatic hydrocarbon, substituted aromatic heterocyclic group, or substituted condensed polycyclic aromatic of Ar1 is a deuterium atom, a fluorine atom, a chlorine atom, cyano, trifluoromethyl, nitro, linear or branched alkyl having 1 to 6 carbon atoms, cycloalkyl having 5 to 10 carbon atoms, linear or branched alkenyl having 2 to 6 carbon atoms, linear or branched alkyloxy having 1 to 6 carbon atoms, cycloalkyloxy having 5 to 10 carbon atoms, phenyl, naphthyl, anthryl, styryl, phenoxy, tolyloxy, benzyloxy, and phenethyloxy, wherein the substituent may be further substituted and wherein two or more substituents may bind to each other via a single bond, substituted or unsubstituted methylene, an oxygen atom, or a sulfur atom to form a ring;

[Chemical Formula 14]

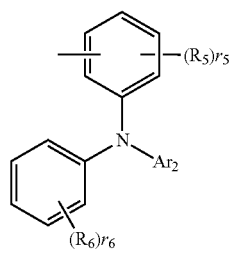

(3)

wherein R5 and R6 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r5 represents 0 or an integer of 1 to 4, r6 represents 0 or an integer of 1 to 5, and Ar2 represents substituted or unsubstituted aromatic hydrocarbon, a substituted or unsubstituted aromatic heterocyclic group, or substituted or unsubstituted condensed polycyclic aromatic;

[Chemical Formula 15]

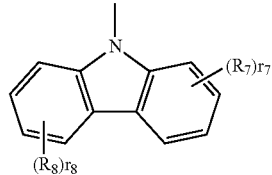

(4)

wherein R7 and R8 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r7 and r8 may be the same or different, and represent 0 or an integer of 1 to 4;

[Chemical Formula 16]

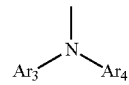

(5)

wherein Ar3 and Ar4 may be the same or different, and represent substituted or unsubstituted aromatic hydrocarbon, a substituted or unsubstituted aromatic heterocyclic group, or substituted or unsubstituted condensed polycyclic aromatic, and these groups may bind to each other via a single bond, substituted or unsubstituted methylene, an oxygen atom, or a sulfur atom to form a ring;

[Chemical Formula 17]

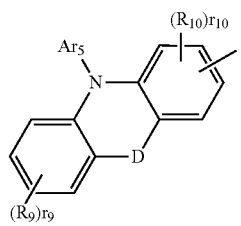

(6)

wherein R9 and R10 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r9 represents 0 or an integer of 1 to 4, r10 represents 0 or an integer of 1 to 3, Ar5 represents substituted or unsubstituted aromatic hydrocarbon, a substituted or unsubstituted aromatic heterocyclic group, or substituted or unsubstituted condensed polycyclic aromatic, and D represents substituted or unsubstituted methylene, an oxygen atom or a sulfur atom

[Chemical Formula 18]

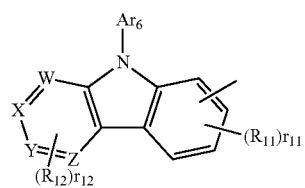

(7)

wherein R11 and R12 may be the same or different, and represent a deuterium atom, a fluorine atom, a chlorine atom, cyano, nitro, linear or branched alkyl having 1 to 6 carbon atoms that may have a substituent, cycloalkyl having 5 to 10 carbon atoms that may have a substituent, linear or branched alkenyl having 2 to 6 carbon atoms that may have a substituent, linear or branched alkyloxy having 1 to 6 carbon atoms that may have a substituent, cycloalkyloxy having 5 to 10 carbon atoms that may have a substituent, substituted or unsubstituted aromatic hydrocarbon, a substituted or unsubstituted aromatic heterocyclic group, substituted or unsubstituted condensed polycyclic aromatic, or substituted or unsubstituted aryloxy, and these substituents may bind to each other via a single bond, substituted or unsubstituted methylene, an oxygen atom, or a sulfur atom to form a ring, and wherein r11 and r12 may be the same or different, and represent 0 or an integer of 1 to 3, Ar6 represents substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom, where only one of W, X, Y, and Z is a nitrogen atom, and, in this case, the nitrogen atom does not have the substituent R12.

8. The organic electroluminescent device according to claim 7, wherein the organic layer is a hole transport layer, and wherein the compound of the general formula (1) is used as at least one constituent material in the hole transport layer.

9. The organic electroluminescent device according to claim 7, wherein the organic layer is an electron blocking layer, and wherein the compound of the general formula (1) is used as at least one constituent material in the electron blocking layer.

10. The organic electroluminescent device according to claim 7, wherein the organic layer is a hole injection layer, and wherein the compound of the general formula (1) is used as at least one constituent material in the hole injection layer.

11. The organic electroluminescent device according to claim 7, wherein the organic layer is a light emitting layer, and wherein the compound of the general formula (1) is used as at least one constituent material in the light emitting layer.

* * * * *